US005114615A

United States Patent [19]

Ishibashi et al.

[11] Patent Number: 5,114,615

[45] Date of Patent: May 19, 1992

[54] LIQUID CRYSTAL COMPOUNDS AND INTERMEDIATES THEREOF

[75] Inventors: Shigeki Ishibashi; Kouzaburou Nakamura; Tohru Maruno, all of Musashino; Masaaki Nakahata, Kawagoe; Takaaki Negishi, Kawagoe; Fumiyoshi Urano, Kawagoe, all of Japan

[73] Assignees: Wako Pure Chemical Industries, Ltd.; Nippon Telegraph and Telephone Corporation, Tokyo, both of Japan

[21] Appl. No.: 765,411

[22] Filed: Sep. 25, 1991

Related U.S. Application Data

[63] Continuation of Ser. No. 225,979, Jul. 29, 1988, abandoned.

[30] Foreign Application Priority Data

Jul. 31, 1987 [JP] Japan ................................ 62-190193

[51] Int. Cl.$^5$ ....................... C09K 19/20; C09K 19/52; C07C 69/76; C07C 41/00

[52] U.S. Cl. .......................... 252/299.67; 252/299.01; 560/64; 560/73; 560/76; 560/85; 568/633

[58] Field of Search ....................... 252/299.01, 299.67; 560/8, 55, 64, 73, 76, 85; 568/633

[56] References Cited

U.S. PATENT DOCUMENTS

| | | | |
|---|---|---|---|
| 3,843,706 | 10/1974 | Weil | 260/458 |
| 3,852,057 | 3/1974 | Findley | 71/78 |
| 4,744,918 | 5/1988 | Heppke et al. | 252/299.65 |

FOREIGN PATENT DOCUMENTS

| | | |
|---|---|---|
| 0110299 | 6/1984 | European Pat. Off. . |
| 0136725 | 4/1985 | European Pat. Off. . |
| 0175591 | 9/1985 | European Pat. Off. . |
| 0168043 | 1/1986 | European Pat. Off. . |
| 63/101483 | 5/1988 | Japan . |
| 63/172788 | 7/1988 | Japan . |
| 63/243062 | 10/1988 | Japan . |
| 2181429 | 4/1987 | United Kingdom . |
| 87/05012 | 8/1987 | World Int. Prop. O. . |

OTHER PUBLICATIONS

Chemical Abstracts, vol. 109, No. 4, Jul. 25th, 1988, p. 536, abstract No. 30825j.

R. B. Meyer et al, "Ferroelectric Liquid Crystals", Journal de Physique (Letters), 36, pp. L69–L71 (1975).

Noel A. Clark et al, "Submicrosecond Bistable Electro-Optic Switching in Liquid Crystals", Appl. Phys. Lett., 36(11), pp. 899–901 (1980).

Taniguchi et al., Jap. J. Applied Physics, vol. 24(4), pp. 452–455 (Apr. 1988).

Taniguchi et al., Ferroelectrics, vol. 77, pp. 137–144 (1988).

*Primary Examiner*—Robert L. Stoll

*Assistant Examiner*—Shean C. Wu

*Attorney, Agent, or Firm*—Armstrong, Nikaido, Marmelstein, Kubovcik & Murray

[57] ABSTRACT

A liquid crystal compound of the formula:

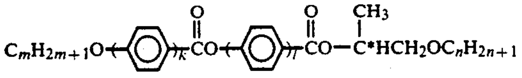

wherein m and n are independently integers of 1 to 22; k and l are independently integers of 1 to 2; and C* is an asymmetric carbon atom, is chemically stable and can be applied to liquid crystal display devices operable at room temperature.

4 Claims, No Drawings

LIQUID CRYSTAL COMPOUNDS AND INTERMEDIATES THEREOF

This application is a continuation of application Ser. No. 225,979 filed Jul. 29, 1988 now abandoned.

BACKGROUND OF THE INVENTION

This invention relates to a liquid crystal compound and an intermediate thereof.

In a modern, highly information-oriented society, innovation in information display technique as well as innovations of information processing, memory and transmission techniques are inevitable. Liquid crystal display devices have been used as digital displays in many applications, such as hand-held calculators, watches, etc., since they have advantages in that it is possible to drive them at low voltage driving (several volts to several tens volts), they consume a small amount of electric power (several $\mu W/cm^2$ to several tens $\mu W/cm^2$), they are excellent in saving energy, they can be made thin and light-weight, they produce hardly any eye fatigue due to a non-emissive type, they are very economical, and the like. Further, they have recently been applied as flat displays for animations, such as television, in combination with active matrix driving circuits such as TFT (thin film transistor).

Most of such liquid crystal display devices now practically used are of the twisted nematic (TN) display mode, which has a defect in that their response speed is as slow as several tens msec. due to the revolution in a plane including a molecular axis by static forces generated by respect to application of a voltage. Therefore, liquid crystals excellent in high speed response properties have been desired.

In order to respond to such a demand, R. B. Meyer et al planned and synthesized p-decyloxybenzylidene p'-amino 2-methyl butyl cinnamate (hereinafter referred to as "DOBAMBC") having an asymmetric carbon atom, and found that DOBAMBC shows a chiral smectic C phase and that the phase is a ferroelectric liquid crystalline phase [R. B. Meyer et al; J. de physique 36, L-69 (1975)]. The response properties of ferroelectric liquid crystals with respect to an electric field E depend on precession for maintaining the tilt angle constant by spontaneous polarization Ps. The driving force PsE is remarkably great compared with a method for applying dielectric anisotropy in nematic liquid crystals.

When a ferroelectric liquid crystal is sandwiched between a pair of electrodes having a gap thinner than the helical pitch after subjected to an orientation treatment, there is formed a molecular configuration state corresponding to a smectic C structure wherein the helical structure disappears. When a d.c. electric field is applied in this case, it is found that bistable states are formed depending on the polarity of the electric field. By applying this memory effect, it is not necessary to use active matrix driving, and display by a simple matrix becomes possible, which results in making it possible to economically produce liquid crystal display devices with high speed response. In practice, high speed response is confirmed by sandwiching a ferroelectric liquid crystal in a very thin cell [N. A. Clark, and S. T. Lagerwall: Appl. Phys. Lett., 36, 899 (1980)].

But DOBAMBC has defects in that its operating temperature is high (Sc* phase temperature : 75° to 95° C.) and its, stability is not sufficient because of hydrolysis.

On the other hand, European Patent Publication Nos. 0110299 and 0136725 disclose compounds of the formula:

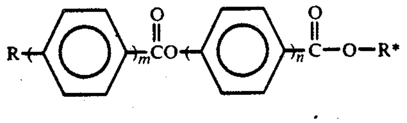

wherein R* is an optically active alkyl group containing an asymmetric carbon atom, said compounds being excellent in stability due to having no azomethine group unlike DOBAMBC. But compounds having a hydrocarbon group as a side chain (which is optically active) generally have a higher liquid crystal phase temperature than those having an ether linkage in the side chain. The compound obtained from lactic acid, as disclosed in European Patent Publication No. 0175591, has an ether linkage outside of an asymmetric carbon atom and is resistant to moisture, but is not sufficiently high in spontaneous polarization since the asymmetric carbon atom is far from an aromatic ring.

SUMMARY OF THE INVENTION

It is an object of this invention to provide a liquid crystal compound which is stable chemically and shows a liquid crystal phase at near room temperature and higher than room temperature, an intermediate thereof, and a process for producing the same.

This invention provides a liquid crystal compound of the formula:

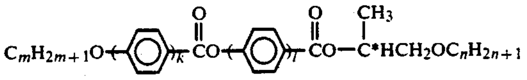 [I]

wherein m is an integer of 1 to 22; n is an integer of 1 to 22; k and l are independently an integer of 1 or 2; and C* is an asymmetric carbon atom.

This invention also provides intermediates for synthesizing such a a liquid crystal compound which are represented by the formulae:

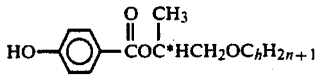

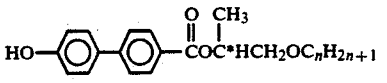

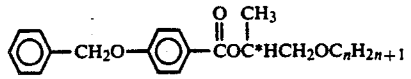

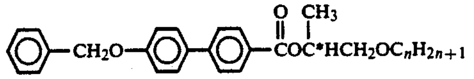

and

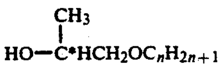

wherein n is an integer of 1 to 22; and C* is an asymmetric carbon atom.

DESCRIPTION OF THE PREFERRED EMBODIMENTS

A molecular structure of ferroelectric liquid crystals comprises terminal flexible portions, a core portion and a chiral carbon portion. The liquid crystal compound of the present invention is characterized by exhibiting a ferroelectric phase at near room temperature or higher and having a high spontaneous polarization due to its having an ester structure in its core portion. Heretofore, as the core portion, there have been used a biphenyl, aromatic ester, heterocyclic, or polycyclic moiety. Further, the chiral carbon portion has been obtained by using amyl alcohol, lactic acid, and an amino acid as a starting material. But there have not been known liquid crystal compounds having an aromatic ester structure as the core portion, and a 1-alkoxy-2-propoxy unit as a chiral portion, which is obtained from ethyl lactate as claimed in the present invention. Because they comprise such a special structure, the liquid crystal compounds of the present invention are chemically stable, and have a ferroelectric phase at near room temperature and higher than room temperature. Further, even if some of the invented compounds do not show a ferroelectric phase near room temperature, a liquid crystal composition showing a ferroelectric phase near room temperature can be obtained by mixing such compounds with one or more other liquid crystal compounds showing, for example, a smectic C phase or a chiral smectic C phase.

The liquid crystal compounds of the present invention are represented by the formula:

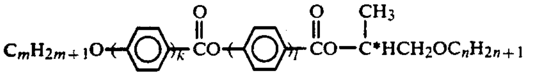
[I]

wherein k is an integer of 1 or 2; l is an integer of 1 or 2; m is an integer of 1 to 22; n is an integer of 1 to 22; and C* is an asymmetric carbon atom.

Preferable examples of the compounds of the formula [I] are as follows:

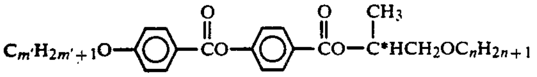
[II]

wherein m' is an integer of 5 to 22; and n and C* are as defined above.

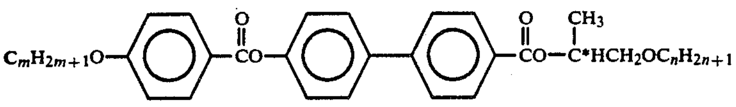
[III]

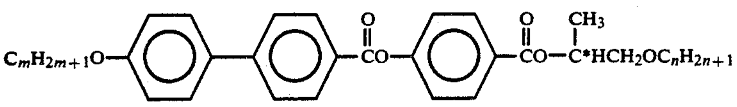
[IV]

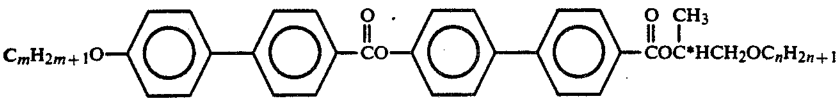
[V]

wherein m, n and C* are as defined above.

The liquid crystal compounds of the formula [I] and intermediates for producing the same can be produced as follows.

First, ethyl lactate is reduced by a reducing agent, such as lithium aluminum hydride or lithium triethylborohydride/lithium borohydride in an organic solvent such as ethyl ether, isopropylether, tetrahydrofuran etc., with cooling to about 25° C. or lower, to S(+)-1,2-propanediol. Then, S(+)-1,2-propanediol is converted to s(+)-2-hydroxypropyl p-toluenesulfonate, using 0.5 to 1.5 equivalents of p-toluenesulfonyl chloride per equivalent of S(+)-1,2-propanediol in a solvent such as pyridine, triethylamine or the like, followed by a reaction with an alcohol in the presence of metallic sodium, metallic potassium, sodium hydride, sodium alcoholate, potassium alcoholate etc., for several hours at a temperature from room temperature to 150° C., to give an intermediate of the formula:

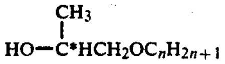
[X]

wherein C* and n are as defined above.

The intermediate of the formula [X] can also be produced as follows:

In order to protect the hydroxyl group of ethyl lactate, 3,4-dihydro-2H-pyran is used to form tetrahydropyranyl ether, which is reduced by lithium aluminum hydride or lithium triethylborohydride/lithium borohydride in a solvent such as ethyl ether, isopropyl ether, tetrahydrofuran, etc., with cooling to about 25° C. or lower to produce S(+)-2-(2-tetrahydropyranyloxy)-propanol. Then, using p-toluenesulfonyl chloride, there is synthesized S(+)-2-(2-tetrahydropyranyloxy) propyl p-toluenesulfonate, which is reacted with an alcohol to produce the intermediate of the formula [X].

A compound of the formula:

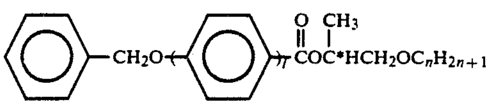
[IX]

wherein n is an integer of 1 to 22; l is an integer of 1 or 2; and C* is an asymmetric carbon, can be produced by reacting the compound of the formula:

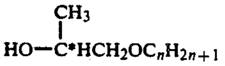
[X]

wherein n and C* are as defined above, with (i) 4-benzyloxybenzoic acid, or a reactive derivative thereof, or (ii) 4-benzyloxybiphenylcarboxylic acid, or a reactive derivative thereof, preferably in an amount of 0.5 to 1.5 equivalents of the latter per equivalent of the compound of the formula [X] in the presence of a base preferably at a temperature from room temperature to a reflux temperature, more preferably 50° C. or lower.

The term "reactive derivative" means an acid chloride, acid anhydride, ester or the like conventionally used in this art. As the base, there can be used pyridine, a tertiary amine such as trimethylamine, N-methylmorpholine, N-methyl pyrrolidine, or the like, an inorganic compound such as sodium hydroxide, potassium hydroxide, sodium carbonate, potassium carbonate, or the like. If necessary, there can be used a solvent such as an aromatic hydrocarbon, e.g. benzene, toluene, etc., a halogenated hydrocarbon, e.g. dichloromethane, dichloroethane, chloroform, carbon tetrachloride, etc.

More specifically, the intermediate of the formula [X] is reacted with 0.5–1.5 equivalents of 4-benzyloxybenzoic acid or a reactive derivative thereof such as an acid chloride thereof to give an intermediate of the formula:

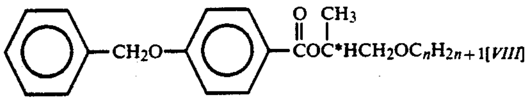

[VIII]

wherein C* and n are as defined above.

Alternatively the intermediate of the formula [X] can be reacted, for example, with 4-benzyloxybenzoyl chloride or 4-[4-(benzyloxyphenyl)benzoyl chloride to give an intermediate of the formula:

[IX]

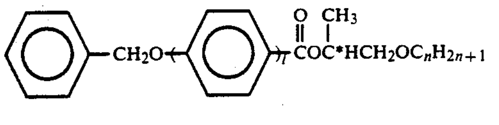

(l = 2)

wherein n and C* are as defined above.

A compound of the formula:

[VII]

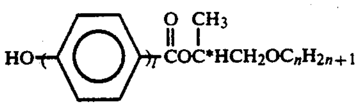

wherein l is an integer of 1 or 2; n is an integer of 1 to 22; and C* is an asymmetric carbon atom, can be produced by reacting the compound of the formula:

[IX]

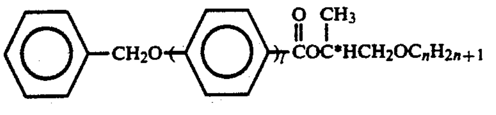

wherein l, n and C* are as defined above with hydrogen in an organic solvent in the presence of a catalyst preferably at a temperature from room temperature to 50° C. under an atmospheric pressure or under pressure, more preferably up to an initial hydrogen pressure of 10 kg/cm$^2$.

As the catalyst, there can be used Raney nickel, 5–10% palladium on carbon, or a mixture thereof.

More specifically, the intermediate of the formula [VIII] is then catalytically reduced by Raney nickel or 5–10% palladium on carbon in an organic solvent such as methanol, ethanol, ethyl acetate, tetrahydrofuran, methylene dichloride, or the like at room temperature to 50° C. to give an intermediate of the formula:

[VI]

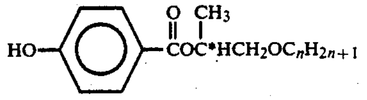

wherein C* and n are as defined above. Alternatively, an intermediate of the formula [IX], wherein l is 2, is subjected to catalytic reduction with Raney nickel or 5–10% palladium or carbon at room temperature to 50° C. to give an intermediate of the formula:

[VII]

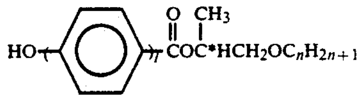

(l = 2)

wherein n and C* are as defined above.

Finally, a liquid crystal compound of the formula:

[I]

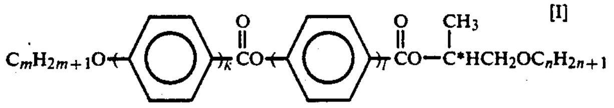

wherein k is an integer of 1 or 2; l is an integer of 1 or 2; m is an integer of 1 to 22; n is an integer of 1 to 22; and C* is an asymmetric carbon atom, can be produced by reacting a compound of the formula:

[VII]

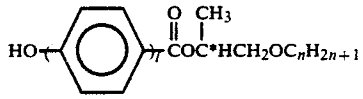

wherein l, n and C* are as defined above, with a (i) 4-alkyloxybenzoic acid or a reactive derivative thereof, or (ii) 4-alkyloxybiphenylcarboxylic acid or a reactive derivative thereof, preferably in an amount of 0.5 to 1.5 equivalents of the latter per equivalent of the compound of the formula [VII], in the presence of a base, preferably at a temperature from room temperature to reflux temperature, more preferably 50° C. or lower.

The term "reactive derivative" means an acid chloride, acid anhydride, ester or the like conventionally used in this art. As the base, there can be used pyridine, a tertiary amine such as trimethylamine, N-methylmorpholine, N-methylpyrrolidine, or the like, an inorganic compound such as sodium hydroxide, potassium hydroxide, sodium carbonate, potassium carbonate, or the like. If necessary, there can be used a solvent, such as an aromatic hydrocarbon, e.g. benzene, toluene, etc., a halogenated hydrocarbon, e.g. dichloromethane, dichloroethane, chloroform, carbon tetrachloride, etc.

More specifically, the intermediate of the formula [VI] or [VII] is then reacted, for example, with a 0.5 to 1.5 equivalents of 4-alkyloxybenzoyl chloride or 4-(4- alkyloxyphenyl) benzoyl chloride in the presence of a base such as pyridine, triethylamine, or the like at room temperature to a reflux temperature to give a liquid crystal compound of the formula [I].

In the case of the liquid crystal compound of the formula:

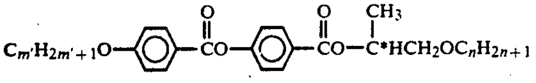

[II]

wherein m', n and C* are as defined above, it can be obtained by reacting an intermediate of the formula [VI] for example, with a 0.5 to 1.5 equivalents of 4-alkyloxybenzoyl chloride in the presence of a base such as pyridine, triethylamine or the like at room temperature to reflux temperature.

As mentioned above, the intermediates of the formulae [X], [VIII], [VI], [IX] and [VII] are usually materials obtained by using ethyl lactate as a starting material for producing the liquid crystal compounds of the formula [I], including preferable examples of the formulae [II], [III], [IV] and [V]. Further, the liquid crystal compounds of the formula [I] can be produced easily and economically.

The present invention is illustrated by way of the following Examples, in which all percents are by weight, unless otherwise specified.

EXAMPLE 1

Synthesis of S(+)-1-Pentyloxy-2-propanol (Compound [X], n=5)

(1) Synthesis of S(−)-Ethyl-2-(2-tetrahydropyranyloxy)propionate

S(−)-Ethyl lactate (88 g, 0.75 mol) was reacted with 3,4-dihydro-2H-pyran (191 g) in the presence of several drops of hydrochloric acid at 25°±5° C. for 12 h with stirring. The reaction mixture was neutralized with potassium carbonate, filtered to remove inorganic materials and then evaporated under reduced pressure. The residue was subjected to fractional distillation to give the title compound as a colorless oil having a 95.3% assay by G. C., area %; yield: 74 g (48.8%); bp 130°-134° C./50 mmHg. $[\alpha]_D^{25}$: −20.8° (Neat).

$^1$H NMR δppm ($CDCl_3$) 1.17 (3H, t, J=6 Hz, —$CH_2C\underline{H}_3$), 1.43 (3H, d, J=6 Hz, —CHC$\underline{H}_3$), 1.53-1.83 (6H, m, THP 3,3-H 4,4-H 5,5-H), 3.37–4.90 (6H, m, —C$\underline{H}$—, —$\underline{CH}_2CH_3$ and THP 2-H 6,6-H).

IR (Neat) νcm$^{-1}$ 2940, 2860, 1750.

(2) Synthesis of S(−)-2-(2-Tetrahydropyranyloxy)propanol

To a solution of lithium aluminum hydride (16.7 g) in dry tetrahydrofuran (600 ml), S(−)-ethyl 2-(2-tetrahydropyranyloxy)propionate (74 g, 0.366 mol), obtained in (1) above, was added dropwise at 10° C. or lower. The resultant mixture was stirred for 1 h at room temperature and then poured into $H_2O$. The mixture was extracted with ethyl ether (3×250 ml), the organic extract was evaporated, and the residue was distilled under reduced pressure to give the title compound as a colorless oil having a 96.7% assay by G. C., area %; yield : 37.6 g (75.2%); bp 110°-130° C./15 mmHg. $[\alpha]_D^{25}$: −28.2° (Neat).

$^1$H NMR δppm ($CDCl_3$) 1.16 (3H, t, J=6 Hz, —C$\underline{H}_3$), 1.40-2.00 (6H, m, THP 3,3-H 4,4-H 5,5-H), 3.36–4.10 (6H, m, —C$\underline{H}$C$\underline{H}_2$O$\underline{H}$ and THP 6,6-H), 4.50–4.90 (1H, m, THP 2-H).

IR (Neat) νcm$^{-1}$: 3450, 2940, 2860.

(3) Synthesis of S(+)-2-(2-Tetrahydropyranyloxy)propyl p-toluenesulfonate

To a S(−)-2-(2-tetrahydropyranyloxy)propanol (37.5 g, 0.237 mol), obtained in (2) above, in pyridine (150 ml), p-toluenesulfonyl chloride (43.5 g) was added at 15° C. or lower, and stirring was continued for 2 h at 10°-15° C. The reaction mixture was evaporated under reduced pressure, the residue was diluted with $H_2O$ and extracted with $CH_2Cl_2$. The organic layer was washed with $H_2O$, dried over $MgSO_4$ and then evaporated. The residue was chromatographed on silica gel (Wako Gel C-200, a trade name, manufactured by Wako Pure Chemical Industries, Ltd.) with n-hexane/$CH_2Cl_2$ (3:1) as eluent to give the title compound as a pale yellow viscous oil; yield : 70 g (94.6%). $[\alpha]_2^{25}$: +4.3° (Neat).

$^1$H NMR δppm ($CDCl_3$) 1.17 (3H, dd, J=6 Hz,

—CHC$\underline{H}_3$), 1.42–1.88 (6H, m, THP 3,3-H 4,4-H 5,5-H), 2.43 (3H, s, Ar—C$\underline{H}$3), 3.48–4.02 (5H, m, —C$\underline{H}$C$\underline{H}_2$— and THP 6,6-H), 4.50–4.60 (1H, m, THP 2-H), 7.27 (2H, d, J=8 Hz, Ar3-H 5-H), 7.83 (2H, d, J=8 Hz, Ar2-H 6-H).

IR (Neat) μcm$^{-1}$: 2960, 2880, 1610.

(4) Synthesis of S(+)-1-Pentyloxy-2-propanol (Compound [X], n=5)

S(+)-2-(2-Tetrahydropyranyloxy)propyl p-toluenesulfonate (40 g, 0.128 mol) obtained in (3) above, was added dropwise to a solution of AmONa[prepared from Na (3.5 g) and amyl alcohol (228 g)] at 60° C. and stirring was continued for 3 h at 60° C. The reaction mixture was taken up in $H_2O$, the organic layer was separated, washed with $H_2O$, dried over $MgSO_4$, and then evaporated under reduced pressure to give a yellow oily product (31 g) as a residue. After dissolving the residue in ethanol (370 ml), hydrochloric acid (7.4 g) was added to the resultant solution and refluxed for 30 min with stirring. The solvent was evaporated under reduced pressure and the residue was distilled under reduced pressure to give the title compound as a colorless oil having a 95.9% assay by G. C. area %; yield : 9.2 g (49.2%); bp 120°-122° C./90 mmHg. $[\alpha]_D^{25}$: +1.0° (Neat)

$^1H$ NMR δppm ($CDCl_3$) 0.90 (3H, t, J=5 Hz, $-(CH_2)_4CH_3$), 1.13 (3H, d, J=6 Hz, $-\overset{|}{C}H-CH_3$), 1.43 (6H, m, $-CH_2-(CH_2)3-CH_3$), 2.87 (1H, s, —OH), 3.47 (4H, m, $-CH_2OCH_2-$), 3.87 (1H, m, $-\overset{|}{C}H-CH_3$).

IR (Neat) νcm$^{-1}$: 3450, 2950, 2870

EXAMPLE 2

Synthesis of S(+)-1-Propyloxy-2-propanol (Compound [X], n=3)

S(+)-2-(2-Tetrahydropyranyloxy)propyl p-toluenesulfonate (47 g, 0.15 mol) obtained in Example 1, (3) was added dropwise to a solution of PrONa [prepared from Na (4.1 g) and n-propyl alcohol (160 ml)] at 60° C. Thereafter, the same procedure as described in Example 1, (4) was followed and distillation was carried out to give the title compound as a colorless oil having a 96.3% assay by G. C., area %; yield: 9.8 g (55.3%); bp 73°-75° C./30 mmHg. $[\alpha]_D^{25}$: +0.23° (Neat).

$^1H$ NMR δppm ($CDCl_3$) 0.93 (3H, t, J=7 Hz, $-CH_2CH_3$), 1.17 (3H, d, J=6 Hz, $-\overset{|}{C}H=CH_3$), 1.54 (2H, m, $-CH_2CH_3$), 2.97 (1H, s, OH), 3.43 (4H, m, $-CH_2OCH_2-$), 3.97 (1H, m, CH).

IR (Neat ) μcm$^{-1}$: 3400, 2955, 2870.

EXAMPLE 3

Synthesis of S(+)-1-Ethyloxy-2-propanol (Compound [X], n=2)

S(+)-2-(2-Tetrahydropyranyloxy)propyl p-toluenesulfonate (47 g, 0.15 mol) obtained in Example 1, (3) was added dropwise to a solution of EtONa [prepared from Na (4.1 g) and ethanol (150 ml)] at 60° C. Thereafter, the same procedure as described in Example 1, step (4) was followed and distillation was carried out to give the title compound as a colorless oil having a 95.9% assay by G. C., area %; yield: 6.2 g (39.7%); bp 52°-54° C./50 mmHg. $[\alpha]_D^{25}$: +4.6° (Neat).

$^1H$ NMR δppm ($CDCl_3$) 1.13 (3H, d, J=7 Hz, $-\overset{|}{C}H-CH_3$), 1.20 (3H, t, J=7 Hz, $-CH_2CH_3$), 2.70 (1H, s, OH), 3.47 (4H, m, $-CH_2OCH2-$), 3.93 (1H, m, CH).

IR (Neat) νcm$^{-1}$: 3400, 2950, 2850.

EXAMPLE 4

Synthesis of S(+)-1-Pentyloxy-2-propanol (Compound [X], n=5)

(1) Synthesis of S(+)-1,2-propanediol

To a solution of lithium aluminum hydride (78 g) in dry tetrahydrofuran (850 ml), S(−)-ethyl lactate (236.6 g, 2 mols) was added dropwise at 10° C. or lower. The resultant mixture was stirred for 1 h at room temperature, then poured into $H_2O$ and filtered to remove inorganic materials. The filtrate was washed with ethyl acetate, the aqueous layer was separated, concentrated under reduced pressure and the residue was distilled under reduced pressure to give the title compound as a colorless oil having a 96.9% assay by G. C., area %; yield: 78.2 g (51.4%); bp 80°-81° C./6 mmHg. $[\alpha_D^{25}$: +16.0° (Neat). IR spectrum of this product was in good agreement with that of a commercially available material.

(2) Synthesis of S(+)-2-Hydroxypropyl p-toluenesulfonate

To a solution of S(+)-1,2-propanediol (78.2 g, 1.03 mol) obtained in above (1) in pyridine (530 ml), p-toluenesulfonyl chloride (167 g) was added at 15° C. or lower and stirring was continued for 4 h at the same temperature. The reaction mixture was evaporated, the residue was diluted with $H_2O$ and extracted with $CH_2Cl_2$. The organic layer was washed with $H_2O$, dried over $MgSO_4$ and then evaporated. The resultant residue was chromatographed on silica gel (Wako Gel C-200, manufactured by Wako Pure Chemical Industries, Ltd.) with $CH_2Cl_2$ as eluent to give the title compound as a pale yellow visous oil; yield: 117 g (58.0%). $[\alpha]_D^{25}$: +4.7° (Neat).

$^1H$ NMR δppm ($CDCl_3$) 1.17 (3H, d, J=6 Hz, $-\overset{|}{C}H-CH_3$), 2.47 (3H, s, Ar—$CH_3$), 2.77 (1H, bs, OH), 3.97 (3H, m, $-\overset{|}{C}H-CH_2-O-$), 7.37 (2H, d, J=8 Hz, Ar 3-H 5-H), 7.83 (2H, d, J=8 Hz, Ar 2-H 6-H).

(3) Synthesis of S(+)-1-Pentyloxy-2-propanol (Compound [X], n=5)

S(+)-2-Hydroxypropyl p-toluenesulfonate (116 g, 0.50 mol) obtained in above (2) was added dropwise to a solution of AmONa [prepared from Na (13.8 g) and amyl alcohol (500 ml)] at 60° C. and stirring was continued for 1 h at 60° C. The reaction mixture was taken up in $H_2O$, the organic layer was separated, washed with $H_2O$, dried over $MgSO_4$, and then evaporated. The residue was distilled under reduced pressure to give the title compound as a colorless oil having a 95.6% assay by G. C., area %; yield: 33.7 g (46.1%); bp 120°-122° C./90 mmHg. $[\alpha]_D^{25}$: +1.0° (Neat)

IR, NMR and optical rotation data of this product were identical with those of the product as described for Example 1.

EXAMPLE 5

Synthesis of S(+)-1-Propyloxy-2-propanol

(Compound [X], n=3)

S(+)-2-Hydroxypropyl p-toluenesulfonate (45 g, 0.195 mol) obtained in Example 4, (2) was added dropwise to a solution of PrONa [prepared from Na (5.3 g) and n-propyl alcohol (150 ml)] at 60° C. Thereafter, the same procedure as described in Example 4, (3) was followed and distillation was carried out to give the title compound as a colorless oil having a 96.0% assay by G. C., area %; yield: 15.0 g (73.9%); bp 73°-75° C./30 mmHg. $[\alpha]_D^{25}$: +0.23° (Neat)

IR, NMR and optical rotation data of this product were identical with those of the product as described for Example 2.

EXAMPLE 6

Synthesis of S(+)-1-Ethyloxy-2-propanol

(Compound [X], n=2)

S(+)-2-Hydroxypropyl p-toluenesulfonate (66 g, 0.285 mol) obtained in Example 4, (2) was added dropwise to a solution of EtONa [prepared from Na (7.6 g) and ethanol (150 ml)] at 60° C. Thereafter, the same procedure as described in Example 4, (3) was followed and distillation was carried out to give the title compound as a colorless oil having a 96.6% assay by G. C., area %; yield: 18.4 g (62.0%); bp 52°-54° C./50 mmHg. $[\alpha]_D^{25}$: +4.6° (Neat).

IR, NMR and optical rotation data of this product were identical with those of the product as described for Example 3.

EXAMPLE 7

Synthesis of S(+)-1-Methyloxy-2-propanol

(Compound [X], n=1)

S(+)-2-Hydroxypropyl p-toluenesulfonate (23.1 g, 0.1 mol) obtained in Example 4, (2) was added dropwise to a solution of 28% sodium methoxide (21.3 g) in methanol (40 ml) at 50° C. and stirring was continued for 1 h at 50° C. The reaction mixture was filtered to remove any insoluble material, evaporated and the residue was subject to fractional distillation to give the title compound as a colorless oil having a 95.5% assay by G. C., area %; yield: 4.1 g (45.5%); bp 86°-87° C. $[\alpha]_D^{25}$: +3.8° (c2, MeOH).

$^1H$ NMR δppm ($CDCl_3$) 1.33 (3H, d, J=6 Hz, $$-\overset{|}{C}H-C\underline{H}_3),$$

3.06 (1H, bs, O$\underline{H}$), 3.30 (3H, s, OC$\underline{H}_3$), 3.57 (2H, d, J=6 Hz, $$-\overset{|}{C}HC\underline{H}_2O-),$$

3.83-3.94 (1H, m, C$\underline{H}$).

IR (Neat) νcm$^{-1}$: 3350, 2950, 2850.

EXAMPLE 8

Synthesis of S(+)-1-Decyloxy-2-propanol

(Compound [X], n=10)

To a suspension of metallic sodium (2.3 g) and decyl alcohol (31.6 g) in xylene (100 ml), S(+)-2-hydroxypropyl p-toluenesulfonate (21.0 g, 0.09 mol) obtained in Example 4, (2) was added dropwise at 90° C., and mixture was stirred for 3 h at 133°-134° C. After cooling, the reaction mixture was taken up in $H_2O$, the organic layer was separated, washed with $H_2O$, dried over $MgSO_4$, and then evaporated. The residue was distilled to give the title compound as a colorless oil having a 97.4% assay by G. C., area %; yield: 6.4 g (32.7%); bp 150°-152° C./18 mmHg. $[\alpha]_D^{25}$: +3.6° (c2, MeOH)

$^1H$ NMR δppm ($CDCl_3$): 0.90 (3H, t, J=6 Hz, $-(CH_2)_8-C\underline{H}_3$), 1.03-1.90 (19H, m, $$-\overset{|}{C}HC\underline{H}_3,$$

$-(CH_2)_8-CH_3$), 2.67 (1H, bs, O$\underline{H}$), 3.20-3.57 (4H, m, $-C\underline{H}_2OC\underline{H}_2-$), 3.73-4.17 (1H, m, $$-\overset{|}{C}\underline{H}CH_3).$$

IR (Neat) νcm$^{-1}$: 3420, 2920, 2850.

EXAMPLE 9

Synthesis of S(+)-1-Pentyloxy-2-propyl 4-benzyloxybenzoate

(Compound [VIII], n=5)

(1) Synthesis of 4-Benzyloxybenzoic acid

Ethyl p-hydroxybenzoate (200 g, 1.2 mol) was reacted with benzyl chloride (190 g, 1.5 mol) and potassium carbonate (165 g) for 12 h under reflux with stirring. After cooling, the mixture was filtered to remove inorganic materials, a half amount of acetone was evaporated, then was taken up in $H_2O$ (1 l) and extracted with $CH_2Cl_2$ (400 ml). The organic extract was washed with $H_2O$, dried over $MgSO_4$ and evaporated to give a yellow viscous oil (400 g) as a residue. Then the residue was stirred in $H_2O$ (1 l) and ethanol (500 ml) containing sodium hydroxide (60 g) for 4 h under reflux. After cooling, the reaction mixture was acidified with hydrochloric acid, the resultant precipitate was filtered, washed with $H_2O$, and recrystallized from ethanol to give the title compound as a white crystals; yield: 195 g (71.2%); mp 191.2°-192.6° C.

$^1H$ NMR δppm ($CDCl_3$-DMSO-$d_6$) 5.08 (2H, s, Ar—C$\underline{H}_2$O—), 6.93 (2H, d, J=8 Hz, Ar 3-H 5-H), 7.37 (5H, s, $\underline{Ar}$H), 7.90 (2H, d, J=8 Hz, Ar2-H 6-H), 8.53 (1H, bs, COOH).

IR (KBr) νcm$^{-1}$: 2900, 2850, 2800, 2650, 2530, 1675, 1605.

(2) Synthesis of S(+)-1-Pentyloxy-2-propyl 4-benzyloxybenzoate (Compound [VIII], n=5)

To a solution of 4-benzyloxybenzoic acid (14.4 g, 63 mmol) obtained in above (1) in 1,2-dichloroethane, thionyl chloride (22.5 g) was added dropwise at 50°-60° C., and stirring was continued for 2 h under reflux. The reaction mixture was evaporated to dryness and the resultant residue was suspended in pyridine (200 ml). To this solution, S(+)-1-pentyloxy-2-propanol (8.8 g, 60 mmol) obtained in Example 1, (4) was added dropwise at 20°-25° C. and stirred for 20 h at 20°-25° C. The reaction mixture was filtered to remove any insoluble material, evaporated, diluted with $H_2O$ and extracted with ethyl ether. The organic extract was evaporated and the resultant residue (15.5 g) was chromatographed on silica gel (Wako Gel C-200) with n-hexane/EtOAc (10:1) as eluent to give the title compound as a pale yellow viscous oil; yield: 9.8 g (45.8%).

$[\alpha]_D^{25}$: +21.8° (c2, MeOH).

$^1H$ NMR δppm ($CDCl_3$) 0.83 (3H, t, J=5 Hz, $-(CH_2)_4-C\underline{H}_3$), 1.30 (3H, d, J=6 Hz, $-\overset{|}{C}H-C\underline{H}_3$), 1.30 (6H, m, $-(C\underline{H}_2)_3-CH_3$), 3.47 (4H, m, J=6 Hz—, $-C\underline{H}_2OC\underline{H}_2-$), 5.70 (2H, s, Ar—$C\underline{H}_2O-$), 5.30 (1H, m, $-\overset{|}{C}\underline{H}-CH_3$), 7.00 (2H, d, J=8 Hz, Ar3-H 5-H), 7.43 (5H, s, ArH), 8.06 (2H, d, J=8 Hz, Ar2-H, 6-H).

IR (Neat) $\nu cm^{-1}$: 2930, 2860, 1710, 1610.

EXAMPLE 10

Synthesis of S(+)-Propyloxy-2-propyl 4-benzyloxybenzoate (Compound [VIII], n=3)

Using 4-benzyloxybenzoic acid (37.7 g, 0.165 mol) obtained in Example 9, (1), 4-benzoyloxy benzoylchloride was produced in the same manner as described in Example 9, (2), and then reacted with S(+)-1-propyloxy-2-propanol (15.0 g, 0.127 mol) obtained in Example 2 in the same manner as described in Example 9, (2) to give the title compound as a pale yellow viscous oil; yield: 21.0 g (50.3%) $[\alpha]_D^{25}$: +26.2° (c2, MeOH).

$^1H$ NMR δppm ($CDCl_3$) 0.80 (3H, t, J=6 Hz, $-CH_2C\underline{H}_3$), 1.33 (3H, d, J=7 Hz, $-\overset{|}{C}H-C\underline{H}_3$), 1.33 (2H, m, $-CH_2C\underline{H}_2CH_3$), 3.43 (4H, m, J=6 Hz, $-C\underline{H}_2OC\underline{H}_2-$), 5.03 (2H, s, Ar—$C\underline{H}_2-$), 5.30 (1H, m, $-\overset{|}{C}\underline{H}-CH_3$), 6.93 (2H, d, J=8 Hz, Ar3-H 5-H), 7.33 (5H, s, ArH), 8.00 (2H, d, J=8 Hz, Ar2-H 6-H).

IR (Neat) $\nu cm^{-1}$: 2975, 2890, 1710, 1610.

EXAMPLE 11

Synthesis of S(+)-Ethyloxy-2-propyl 4-benzyloxybenzoate

(Compound [VIII], n=2)

Using 4-benzyloxybenzoic acid (52.5 g, 0.23 mol) obtained in Example 9, (1), 4-benzyloxybenzoylchloride was produced in the same manner as described in Example 9, (2), and then reacted with S(+)-1-ethyloxy-2-propanol (18.4 g, 0.177 mol) obtained in Example 3 in the same manner as described in Example 9, (2) to give the title compound as a pale yellow viscous oil; yield: 28.5 g (51.2%). $[\alpha]_D^{25}$: +22.1° (c2, MeOH).

$^1H$ NMR δppm ($CDCl_3$) 1.16 (3H, t, J=7 Hz, $-CH_2C\underline{H}_3$), 1.33 (3H, d, J=6 Hz, $-\overset{|}{C}H-C\underline{H}_3$), 3.50 (4H, m, J=6 Hz, $-C\underline{H}_2OC\underline{H}_2-$), 5.03 (2H, s, Ar—$C\underline{H}_2-$), 5.30 (1H, m, $-\overset{|}{C}\underline{H}-$), 6.87 (2H, d, J=8 Hz, Ar3-H 5-H), 7.30 (5H, s, ArH), 7.83 (2H, d, J=8 Hz, Ar 2-H 6-H).

IR (Neat) $\nu cm^{-1}$: 2980, 2880, 1710, 1610.

EXAMPLE 12

Synthesis of S(+)-1-Methyloxy-2-propyl 4-benzyloxybenzoate (Compound [VIII], n=1)

Using 4-benzyloxybenzoic acid (11.6 g, 0.051 mol) obtained in Example 9, (1), 4-benzyloxybenzoyl chloride was produced in the same manner as described in Example 9, (2), and then reacted with S(+)-1-methyloxy-2-propanol (2.6 g, 0.029 mol) obtained in Example 7 in the same manner as described in Example 9, (2) to give the title compound as a pale yellow viscous oil; yield: 4.5 g (63.4%). $[\alpha]_D^{25}$: +16.4° (cl, MeOH).

$^1H$ NMR δppm ($CDCl_3$) 1.36 (3H, d, J=6 Hz, $-\overset{|}{C}H-C\underline{H}_3$), 3.37 (3H, s, $OC\underline{H}_3$), 3.57 (2H, d, J=6 Hz, $-\overset{|}{C}HC\underline{H}_2-$), 5.07 (2H, s, Ar—$C\underline{H}_2-$), 5.05-5.53 (1H, m, J=6 Hz, $-\overset{|}{C}\underline{H}-CH_2-$), 6.97 (2H, d, J=9 Hz, Ar3-H 5-H), 7.37 (5H, s, ArH), 8.00 (2H, d, J=9 Hz, Ar2-H 6-H).

IR (Neat) $\nu cm^{-1}$: 2980, 2930, 2880, 1780, 1700, 1605

EXAMPLE 13

Synthesis of S(+)-1-Decyloxy-2-propyl 4-benzyloxybenzoate (Compound [VIII], n=10)

Using 4-benzyloxybenzoic acid (6.3 g, 0.028 mol) obtained in Example 9,(1), 4-benzyloxybenzoyl chloride was produced in the same manner as described in Example 9 (2), and then reacted with S(+)-1-decyloxy-2-propanol (6.0 g, 0.028 mol) obtained in Example 8 in the same manner as described in Example 9, (2) to give the title compound as a pale yellow viscous oil; yield: 8.5 g (71.4%). $[\alpha]_D^{25}$: +17.6° (c2, MeOH).

$^1$H NMR δppm ($CDCl_3$) 0.87 (3H, t, J=6 Hz, —$(CH_2)_9$—$C\underline{H}_3$), 1.03-1.90 (19H, m,

|
—CH—$C\underline{H}_3$—,

—$CH_2(C\underline{H}_2)_8CH_3$), 3.36-3.57 (4H, m, —$C\underline{H}_2OC\underline{H}_2$—), 5.06 (2H, s, Ar—$C\underline{H}_2$—), 5.03-5.50 (1H, m, J=6 Hz,

|
—C$\underline{H}$—), 6.93 (2H, d, J=9 Hz, Ar3-H 5-H), 7.33 (5H, s, ArH), 7.97 (2H, d, J=9 Hz, Ar2-H 6-H).

IR (Neat) $\nu cm^{-1}$: 2950, 2870, 1715, 1610.

EXAMPLE 14

Synthesis of S(+)-1-Ethyloxy-2-propyl 4-(4-benzyloxyphenyl)benzoate (Compound [IX], n=2)

(1) Synthesis of 4-(4-Benzyloxyphenyl)benzoic acid

To a suspension of 60% sodium hydride (6 g) in dimethylformamide (DMF), ethyl 4-(4-hydroxyphenyl)-benzoate (29.0 g, 0.12 mol) was added in small portions. The mixture was stirred for 15 min and then treated dropwise with benzyl solution was stirred for 6 h under reflux. After cooling, the reaction mixture was taken up in $H_2O$, extracted with ethyl acetate, the organic extract was washed with $H_2O$ and then dried over $MgSO_4$. The solvent was evaporated to give a pale yellow solid (30 g) as a residue. The residue was stirred in $H_2O$ (150 ml) and ethanol (400 ml) containing sodium hydroxide (7.2 g) for 6 h under reflux. After cooling, the reaction mixture was acidified with hydrochloric acid, the resultant precipitate was filtered, washed with $H_2O$ and warm ethanol to give the title compound as a white crystals; yield: 24 g (65.8%); mp 263.0°-265.0° C.

$^1$H NMR δppm ($CDCl_3$-DMSO-$d_6$) 5.17 (2H, s, Ar—$C\underline{H}_2$—), 7.06-8.10 (14H, m, ArH and —COOH).

IR (KBr) $\nu cm^{-1}$: 3100, 2950, 2750, 1700, 1625.

(2) Synthesis of S(+)-1-Ethyloxy-2-propyl 4-(4-benzyloxyphenyl)benzoate (Compound [IX], n=2)

To a solution of 4-(4-benzyloxyphenyl)benzoic acid (18.0 g, 59 mmol) obtained in above (1) in toluene (50 ml), thoinyl chloride (21.1 g) was added dropwise at 50°-60° C., and then stirring was continued for 6 h at 90°-100° C. The mixture was evaporated to dryness and the resultant residue was suspended in pyridine (120 ml). To this solution, S(+)-1-ethyloxy-2-propanol (4.3 g, 57 mmol) obtained in Example 3 was added dropwise at 20°-25° C. and stirred for 8 h at 20°-25° C. The reaction mixture was concentrated, diluted with $H_2O$ and extracted with $CH_2Cl_2$. The organic extract was washed with $H_2O$, evaporated and the resultant residue (23 g) was chromatographed on silica gel (Wako Gel C-200, manufactured by Wako Pure Chemical Industries, Ltd.) with n-hexane/$CH_2Cl_2$ (3:1) as eluent to give the title compound as a pale yellow crystals; yield: 18.8 g (84.5%); mp 77.0°-78.5° C. $[\alpha]_D^{25}$: +21.3° (c2, $CHCl_3$)

$^1$H NMR δppm ($CDCl_3$) 1.17 (3H, t, J-7 Hz, —$OCH_2C\underline{H}_3$), 1.37 (3H, d, J=7 Hz,

|
—CH—$C\underline{H}_3$), 3.27-3.73 (4H, m, —$C\underline{H}_2OC\underline{H}_2$—), 5.07 (2H, s, Ar—$C\underline{H}_2$—), 5.07-5.53 (1H, m, J=6 Hz,

|
—C$\underline{H}$—), 6.93-8.13 (13H, m, ArH).

IR (KBr) $\nu cm^{-1}$: 2950, 2850, 1700, 1600.

EXAMPLE 15

Synthesis of S(+)-1-Pentyloxy-2-propyl 4-hydroxybenzoate (Compound [VI], n=5)

S(+)-1-Pentyloxy-2-propyl 4-benzyloxybenzoate (4.6 g, 13 mmol) obtained in Example 9, (2) was reduced with hydrogen in the presence of 5% palladium on carbon (2 g) in ethyl acetate (150 ml) at 25° C. and 1 atm. After absorbing a theoretical amount of hydrogen, the catalyst was filtered, the solvent was evaporated and the resultant residue (3.2 g) was chromatographed on silica gel (Wako Gel C-200) with n-hexane/ethyl acetate (10:1) as eluent to give the title compound as a colorless viscous oil; yield: 3.0 g (86.6%). $[\alpha]_D^{25}$: +32.2° (c2, MeOH).

$^1$H NMR δppm ($CDCl_3$); 0.86 (3H, t, J=5 Hz, —$(CH_2)_4C\underline{H}_3$) 1.36 (3H, d, J=6 Hz,

|
—CH—$C\underline{H}_3$), 1.36 (6H, m, —$CH_2(C\underline{H}_2)_3CH_3$), 3.53 (4H, m, —$C\underline{H}_2OC\underline{H}_2$—), 5.30 (1H, m,

|
—C$\underline{H}$—), 6.80 (2H, d, J=8 Hz, Ar3-H 5-H), 7.20 (1H, bs, Ar-O$\underline{H}$), 7.87 (2H, d, J=8 Hz, Ar2-H 6-H).

IR (Neat) $\nu cm^{-1}$: 3300, 2940, 2870, 1690, 1610.

EXAMPLE 16

Synthesis of S(+)-1-Propyloxy-2-propyl 4-hydroxybenzoate (Compound [VI], n=3)

S(+)-1-Propyloxy-2-propyl 4-benzyloxybenzoate (20 g, 0.06 mol) obtained in Example 10 was reduced with hydrogen in the presence of Raney nicked (1 g) in methanol (300 ml) at 25° C. and 1 atm. Thereafter, the same procedure as described in Example 10 to give the title compound as a colorless viscous oil; yield: 14.0 g (97.8%). $[\alpha]_D^{25}$: +31.0° (c2, MeOH).

$^1$H NMR δppm ($CDCl_3$) 0.88 (3H,, t, J=7 Hz, —$CH_2C\underline{H}_3$), 1.33 (3H, d, J=6 Hz,

|
—CH—$C\underline{H}_3$), 1.50 (2H, m, —$C\underline{H}_2CH_3$), 3.56 (4H, m, —$C\underline{H}_2OC\underline{H}_2$—), 5.33 (1H, m,

—CH—), 6.83 (2H, d, J=8 Hz, Ar3-H 5-H), 7.93 (2H, d, J=8 Hz, Ar2-H 6-H), 7.93 (1H, s, Ar-OH)

IR (Neat) νcm$^{-1}$: 3320, 2960, 2880, 1710, 1610.

EXAMPLE 17

Synthesis of S(+)-1-Ethyloxy-2-propyl 4-hydroxybenzoate (Compound [VI], n=2)

Using S(+)-1-ethyloxy-2-propyl 4-benzyloxybenzoate (28.0 g, 0.09 mol) obtained in Example 11, reduction was carried out in the same manner as described in Example 15 to afford the title compound as a colorless viscous oil; yield 19.0 g (94 0%) $[\alpha]_D^{25}$: +26.2° (c2, MeOH).

$^1$H NMR δppm ($CDCl_3$): 1.23 (3H,, t, J=7 Hz, —$CH_2CH_3$), 1.38 (3H, d, J=6 Hz,

—CH—$CH_3$), 3.56 (4H, m, —$CH_2OCH_2$—), 5.33 (1H, m,

—CH—), 6.93 (2H, d, J=8 Hz, Ar3-H 5-H), 6.93 (1H, s, Ar-OH), 7.97 (2H, d, J=8 Hz, Ar2-H 6-H)

IR (Neat) νcm$^{-1}$: 3300, 2980, 2880, 1710, 1610.

EXAMPLE 18

Synthesis of S(+)-1-Methyloxy-2-propyl 4-hydroxybenzoate (Compound [VI], n=1)

Using S(+)-1-methyloxy-2-propyl 4-benzyloxybenzoate (4.5 g, 15 mmol) obtained in Example 12, reduction was carried out in the same manner as described in Example 15 to afford the title compound as a colorless visous oil; yield 2.6 g (82.5%). $[\alpha]_D^{25}$: +19.2° (cl, MeOH).

$^1$H NMR δppm ($CDCl_3$): 1.36 (3H, d, J=6 Hz,

—CH—$CH_3$), 3.30 (3H, s, $OCH_3$), 3.60 (2H, d, J=6 Hz, —$CH_2O$—), 4.63 (1H, s, Ar-OH), 5.03–5.53 (1H, m, J=6 Hz,

—CH—), 6.87 (2H, d, J=9 Hz, Ar3-H 5-H), 7.93 (2H, d, J=9 Hz, Ar2-H 6-H).

IR (Neat) νcm$^{-1}$: 3250, 2980, 2930, 1685, 1605

EXAMPLE 19

Synthesis of S(+)-1-Decyloxy-2-propyl 4-hydroxybenzoate (Compound [VI]. n=10)

Using S(+)-1-decyloxy-2-propyl 4-benzyloxybenzoate (8.5 g, 20 mmol) obtained in Example 13, reduction was carried out in the same manner as described in Example 15 to afford the title compound as a colorless viscous oil; yield: 6.2 g (92.1%). $[\alpha]_D^{25}$: +14.3° (c2, $CHCl_3$)

$^1$H NMR δppm ($CDCl_3$) 0.87 (3H, t, J=6 Hz, —$(CH_2)_9CH_3$), 1.03–1.90 (19H, m,

—CH—$CH_3$—,

—$CH_2(CH_2)_8CH_3$), 3.33–3.63 (4H:, m, —$CH_2OCH_2$), 5.10–5.57 (1H, m,

—CH—), 6.83 (2H, d, J=9 Hz, Ar3-H 5-H), 7.87 (3H, d, J=9 Hz, Ar2-H 6-H and Ar-OH).

IR (Neat) νcm$^{-1}$: 3350, 2940, 2860, 1715, 1680, 1610.

EXAMPLE 20

Synthesis of S(+)-1-Ethyloxy-2-propyl 4-(4-hydroxyphenyl)benzoate (Compound [VII], n=2)

Using S(+)-1-ethyloxy-2-propyl 4-(4-benzyloxyphenyl)benzoate (18.0 g, 46 mmol) obtained in Example 14, reduction was carried out in the same manner as described in Example 15 to give the title compound as white crystals; yield: 13.5 g (97.8%); mp 82.5°–86.5° C. $[\alpha]_D^{25}$: +22.9° (c2, $CHCl_3$)

$^1$H NMR δppm ($CDCl_3$) 1.23 (3H, t, J=7 Hz, —$CH_2CH_3$), 1.30 (3H, d, J=6 Hz,

—CH—$CH_3$), 3.47–3.83 (4H, m, —$CH_2OCH_2$—), 5.10–5.57 (1H, m, J=6 Hz,

—CH—), 6.83–8.13 (9H, m, ArH and Ar—OH).

IR (KBr) νcm$^{-1}$: 3250, 2950, 2860, 1700, 1600.

EXAMPLE 21

Synthesis of S(+)-1-Pentyloxy-2-propyl 4-(4-decyloxybenzoyloxy)benzoate (Compound [II], m'=10, n=5)

(1) Synthesis of 4-Decyloxybenzoic acid

To a solution of decyl bromide (66.7 g, 0.3 mol), potassium carbonate (41.5 g) and sodium iodide (45.0 g) in acetone (500 ml), ethyl p-hydroxy benzoate (41.5 g, 0.25 mol) was added and stirring was continued for 24 h under reflux. After cooling, the reaction mixture was filtered to remove inorganic materials, taken up in $H_2O$ (1 l) and extracted with $CH_2Cl_2$ (2×100 ml). The organic layer was separated, washed with $H_2O$, dried over $MgSO_4$, and evaporated to give a yellow visous oil (86 g) as a residue. The residue was stirred in $H_2O$ (300 ml) and ethanol (200 ml) containing sodium hydroxide (18 g) for 6 h under reflux. After cooling, the reaction mixture was acidified with hydrochloric acid, the resultant precipitate was filtered, washed with $H_2O$ and recrystallized from ethanol to give the title compound as white microneedles; yield: 28.5 g (40.8%); mp 95.2°-97.4° C. (the 1st mp), 122.8°-124.4° C. (the 2nd mp).

$^1H$ NMR δppm (DMSO-$d_6$): 0.87-2.06 (19H, m, $(C\underline{H}_2)_8-C\underline{H}_3$), 3.97 (2H, t, J=6 Hz, $-C\underline{H}_2O-$), 6.88 (2H, d, J=8 Hz, Ar3-H 5-H), 7.90 (2H, d, J=8 Hz, Ar2-H 6-H), 8.53 (1H, bs, $-COO\underline{H}$).

IR (KBr) νcm$^{-1}$: 2925, 2850, 2650, 2550, 1680, 1605.

(2) Synthesis of S(+)-1-Pentyloxy-2-propyl 4-(4-decyloxybenzoyloxy)benzoate (Compound [II], m'=10, n=5)

To a solution of 4-decyloxybenzoic acid (3.65 g, 13 mmol) obtained in above (1) in 1,2-dichloroethane, thionyl chloride (3.1 g) was added dropwise at 50°-60° C., and then stirring was continued for 2 h under reflux. The mixture was evaporated to dryness and the resultant residue was suspended in pyridine (50 ml). To this solution, S(+)-1-pentyloxy-2-propyl 4-hydroxybenzoate (2.9 g, 11 mmol) obtained in Example 10 was added dropwise at 20°-25° C. and stirred for 20 h at 20°-25° C. The reaction mixture was concentrated, diluted with $H_2O$ and extracted with $CH_2Cl_2$. The organic layer was separated, washed with $H_2O$, dried over $MgSO_4$, and evaporated. The resultant residue (6.1 g) was chromatographed on silica gel (Wako Gel C-200) with n-hexane/ethyl acetate (10:1) as eluent to give a pale yellow solid (4.5 g). The solid was recrystallized thrice from ethanol to give the title compound as a white amorphous powder; yield: 3.6 g (62.1%); mp 41.5°-41.9° C. $[\alpha]_D^{25}$: +11.7° (c2, $CHCl_3$)

$^1H$ NMR δppm ($CDCl_3$) 0.83 (6H, t, $-(CH_2)_9C\underline{H}_3$ and $-(CH_2)_4C\underline{H}_3$), 1.32 (25H, m, $-CH_2(C\underline{H}_2)_8CH_3$,

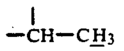

and $-OCH_2(C\underline{H}_2)_3CH_3$), 3.50 (4H, m, $-C\underline{H}_2OC\underline{H}_2-$), 4.13 (2H, t, $-OC\underline{H}_2(CH_2)_8CH_3$), 5.33 (1H, m,

6.87 (2H, d, J=8 Hz,

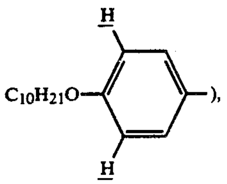

-continued 7.23(2H, d, J=8Hz,

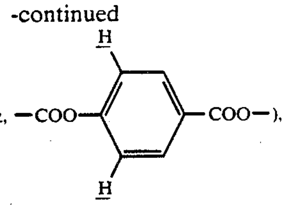

8.10(4H, d, J=8Hz,

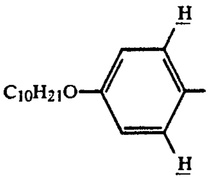

and

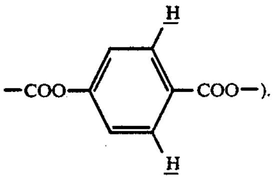

IR (KBr) νcm$^{-1}$: 2940, 2870, 1730, 1715, 1610.

Anal. calcd. for $C_{32}H_{46}O_6$: C%, 72.97; H%, 8.80; Found: C%, 73.05; H%, 8.76.

EXAMPLE 22

Synthesis of S(+)-1-Propyloxy-2-propyl 4-(4-decyloxybenzoyloxy)benzoate (Compound [II], m'=10, n=3)

Using 4-decyloxybenzoic acid (3.65 g, 13 mmol) obtained in Example 21, (1), 4-decyloxybenzoyl chloride was produced in the same manner as described in Example 21, (2), and then reacted with S(+)-1-propyloxy-2-propyl 4-hydroxybenzoate (2.6 g, 11 mmol) obtained in Example 16 in the same manner as described in Example 21, (2) to give the title compound as a white amorphous powder; yield: 4.3 g (78.4%); mp 39.4°-41.8° C. $[\alpha]_D^{25}$: +12.1° (c2, $CHCl_3$).

$^1$NMR δppm ($CDCl_3$) 0.90 (6H, t, $-(CH_2)_9C\underline{H}_3$ and $-OCH_2CH_2C\underline{H}_3$), 1.13 (21H, m, $-OCH_2(C\underline{H}_2)_8CH_3$,

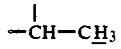

and $-OCH_2C\underline{H}_2CH_3$),3.53 (4H, m, $-C\underline{H}_2OC\underline{H}_2-$), 4.10 (2H, t, $-OC\underline{H}_2(CH_2)_8CH_3$), 5.33 (1H, m,

7.00 (2H, d, J=8 Hz,

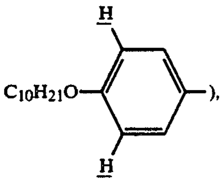

7.33 (2H, d, J=8 Hz,

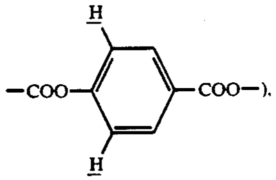

8.17 (4H, d, J=8 Hz,

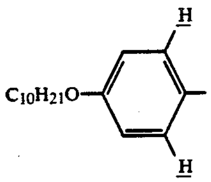

and

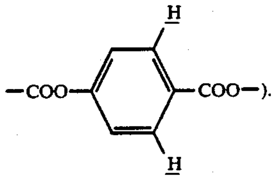

IR (Neat) $\nu cm^{-1}$: 2930, 2870, 1740, 1605.

Anal. calcd. for $C_{30}H_{42}O_6$: C%, 72.26; H%, 8.49; Found: C%, 72.27; H%, 8.44.

EXAMPLE 23

Synthesis of S(+)-1-Ethyloxy-2-propyl 4-(4-decyloxybenzoyloxy)benzoate (Compound [II], m'=10, n=2)

Using 4-decyloxybenzoic acid (3.65 g, 13 mmol) obtained in Example 21, (1), 4-decyloxybenzoyl chloride was produced in the same manner as described in Example 21, (2), and then reacted with S(+)-1-ethyloxy-2-propyl 4-hydroxybenzoate (2.5 g, 11 mmol) obtained in Example 17 in the same manner as described in Example 21, (2) to give the title compound as a white amorphous powder; yield: 3.7 g (69.4%); mp 34.2°-37.8° C. $[\alpha]_D^{25}$: +11.6° (c2, $CHCl_3$)

$^1$H NMR δppm ($CDCl_3$) 0.87 (6H, t, $-(CH_2)_9C\underline{H}_3$ and $-OCH_2C\underline{H}_3$), 1.30 (19H, m, $-OCH_2(C\underline{H}_2)_8CH_3$ and

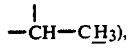

3.56 (4H, n, $-C\underline{H}_2OC\underline{H}_2-$), 4.00 (2H, t, $-OC\underline{H}_2(CH_2)_8CH_3$), 5.27 (1H, m,

6.93 (2H, d, J=8 Hz,

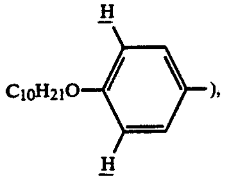

7.33 (2H, d, J=8 Hz,

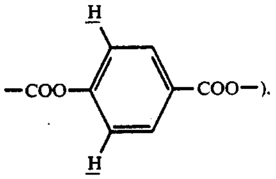

8.07 (4H, d, J=8 Hz,

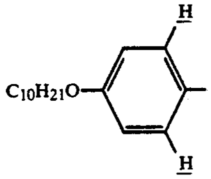

and

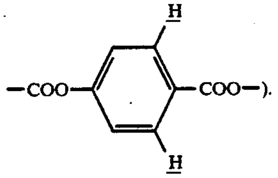

IR (Neat) $\nu cm^{-1}$: 2930, 2855, 1735, 1720, 1605

Anal calcd. for $C_{29}H_{40}O_6$: C%, 71.87; H%, 8.32; Found: C%, 71.90; H%, 8.26.

EXAMPLE 24

Synthesis of S(+)-1-Pentyloxy-2-propyl 4-(4-octyloxybenzoyloxy)benzoate (Compound [II], m'=8, n=5)

(1) Synthesis of 4-Octyloxybenzoic acid

Using ethyl p-hydroxybenzoate (36.7 g, 0.22 mol) and n-octyl bromide (50 g, 0.26 mol), the reaction was carried out in the same manner as described in Example 13, (1), and then recrystallized from ethanol to give the title compound as a white micro-needles; yield: 43.0 g (71.6%); mp 100.2°-101.4° C. (the 1st mp), 107.0°-107.6° C. (the 2nd mp).

[1]NMR δppm (DMSO-$d_6$) 0.90-2.00 (15H, m, $-(C\underline{H}_2)_6C\underline{H}_3$), 4.00 (2H, t, J=6 Hz, $-C\underline{H}_2O-$), 6.90 (2H, d, J=8 Hz, Ar 3-H 5-H), 8.00 (2H, d, J=8 Hz, Ar2-H 6-H), 8.00 (1H, bs, $-COO\underline{H}$).

IR (KBr) $\nu cm^{-1}$: 2940, 2855, 2670, 2550, 1685, 1605.

(2) Synthesis of S(+)-1-Pentyloxy-2-propyl 4-(4octyloxybenzoyloxy)benzoate (Compound [II], m'=8, n=5)

Using 4-octyloxybenzoic acid (3.25 g, 13 mmol) obtained in above (1), 4-octyloxybenzoyl chloride was produced in the same manner as described in Example 21, (2), and then reacted with S(+)-1-pentyloxy-2-propyl 4-hydroxybenzoate (2.9 g, 11 mmol) obtained in Example 15 in the same manner as described in Example 21 (2) to give the title compound as a white amorphous powder; yield: 3.8 g (69.3%); mp 29.0°-30.5° C., $[\alpha]_D^{25}$: +12.1° (c2, $CHCl_3$).

$^1$H NMR δppm ($CDCl_3$) 0.90 (6H, t, $-(CH_2)_7C\underline{H}_3$ and $-O(CH_2)_4CH_3$), 1.30 (21H, m, $-OCH_2(C\underline{H}_2)_6CH_3$,

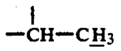

and $-OCH_2(C\underline{H}_2)_3CH_3$), 3.53 (4H, m, $-C\underline{H}_2OC\underline{H}_2-$), 4.06 (2H, t, $-OC\underline{H}_2(CH_2)_6CH_3$), 5.33 (1H, m,

6.97 (2H, d, J=8 Hz,

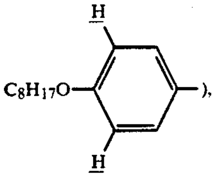

7.30(2H, d, J=8Hz,

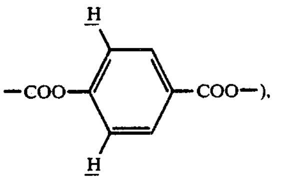

8.16(4H. d. J=8Hz.

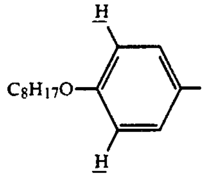

and

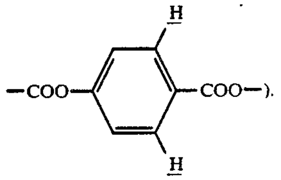

IR (Neat) νcm$^{-1}$: 2920, 2850, 1735, 1710, 1600

Anal. calcd. for $C_{30}H_{42}O_6$: C%, 72.26; H%, 8.49; Found: C%, 72.29; H%, 8.50.

EXAMPLE 25

Synthesis of S(+)-1-Propyloxy-2-propyl 4-(4-octyloxybenzoyloxy)benzoate (Compound [II], m'=8, n=3)

Using 4-octyloxybenzoic acid (3.25 g, 13 mmol) obtained in Example 24, (1), 4-octyloxybenzoyl chloride was produced in the same manner as described in Example 21, (2), and then reacted with S(+)-1-propyloxy-2-propyl 4-hydroxybenzoate (2.6 g, 11 mmol) obtained in Example 16 in the same manner as described in Example 21, (2) to give the title compound as a white amorphous powder; yield: 3.0 g (58.0%); mp 32.8°-36.5° C. $[\alpha]_D^{25}$: +11.3° (c2, $CHCl_3$)

$^1$H NMR δ ($CDCl_3$) 0.90 (6H, t, —$(CH_2)_7C\underline{H}_3$ and —$OCH_2CH_2C\underline{H}_3$), 1.33 (17H, m, —$OCH_2(C\underline{H}_2)_6CH_3$,

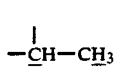

and —$OCH_2C\underline{H}_2CH_3$), 3.56 (4H, m, —$C\underline{H}_2OC\underline{H}_2$—), 4.05 (2H, t, —$OC\underline{H}_2(CH_2)_6CH_3$), 5.33 (1H, m,

6.97 (2H, d, J=8 Hz,

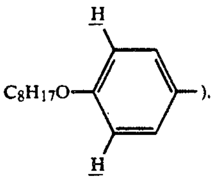

7.30(2H, d, J=8Hz,

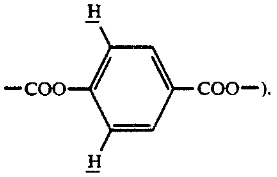

8.10 (4H, d, J=8Hz,

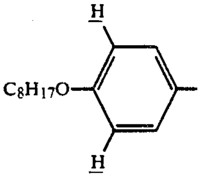

and

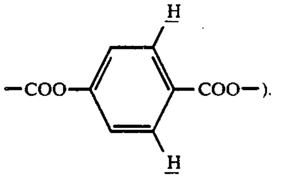

IR (Neat) νcm$^{-1}$: 2925, 2855, 1735, 1720, 1605.

Anal. calcd. for $C_{28}H_{36}O_6$: C%, 71.46; H%, 8.14; Found: C%, 71.50, H%, 8.10.

EXAMPLE 26

Synthesis of S(+)-1-Ethyloxy-2-propyl 4-(4-octyloxybenzoyloxy)benzoate (Compound [II], m'=8, n=2)

Using 4-octyloxybenzoic acid (3.25 g, 13 mmol) obtained in Example 24, (1), 4-octyloxybenzoyl chloride was produced in the same manner as described in Example 21 (2), and then reacted with S(+)-1-ethyloxy-2-propyl 4-hydroxybenzoate (2.5 g, 11 mmol) obtained in Example 17 in the same manner as described in Example 21 (2) to give the title compound as a white leaflets; yield: 4.0 g (79.6%); mp 40.2°-43.3° C. $[\alpha]_D^{25}$: +12.0° (c2, $CHCl_3$)

$^1$H NMR δppm ($CDCl_3$) 0.87 (6H, t, —$(CH_2)_7C\underline{H}_3$ and $OCH_2C\underline{H}_3$), 1.30 (15H, m, —$OCH_2(C\underline{H}_2)_6CH_3$ and

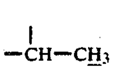

3.56 (4H, m, —$C\underline{H}_2OC\underline{H}_2$), 4.00 (2H, t, —$OC\underline{H}_2(CH_2)_6CH_3$), 5.30 (1H, m,

6.93 (2H, d, J=8Hz,

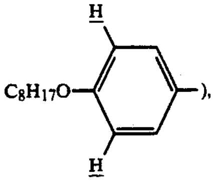

7.27 (2H, d, J=8Hz,

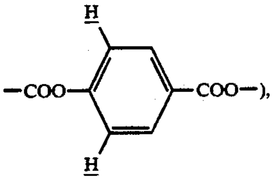

8.10 (4H, d, J=8Hz,

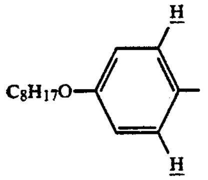

and

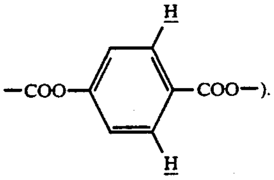

IR (Neat) νcm−1: 2930, 2855, 1735, 1720, 1605.

Anal. calcd. for $C_{27}H_{36}O_6$: C%, 71.03; H%, 7.95; Found: C%, 71.11; H%, 7.93.

EXAMPLE 27

Synthesis of S(+)-1-Pentyloxy-2-propyl 4-(4-heptyloxybenzoyloxy)benzoate (Compound [II], m'=7, n=5)

(1) Synthesis of 4-Heptyloxybenzoic acid

Using ethyl p-hydroxybenzoate (33.3 g, 0.20 mol) and n-heptyl bromide (39.4 g, 0.22 mol), the reaction was carried out in the same manner as described in Example 21, (1), and then recrystallized from ethanol to give the title compound as a white microneedles; yield: 19.0 g (40.2%); mp 86.2°-90.3° C.

$^1$H NMR δppm (DMSO-d$_6$) 0.80-2.10 (13H, m, —(C<u>H</u>$_2$)$_5$—CH$_3$), 4.03 (2H, t, J=6 Hz, —C<u>H</u>$_2$O—), 6.93 (2H, d, J=8 Hz, Ar3-H 5-H), 8.00 (2H, d, J=8 Hz, Ar2-H 6-H), 8.00 (1H, bs, —COO<u>H</u>)

IR (KBr) νcm−1: 2900, 2830, 2640, 2520, 1670, 1600.

(2) Synthesis of S(+)-1-Pentyloxy-2-propyl 4-(4-heptyloxybenzoyloxy)benzoate (Compound [II], m'=7, n=5)

Using 4-heptyloxybenzoic acid (3.07 g, 13 mmol) obtained in above (1), 4-heptyloxybenzoyl chloride was produced in the same manner as described in Example 21, (2), and then reacted with S(+)-1-pentyloxy-2-propyl 4-hydroxybenzoate (2.9 g, 11 mmol) obtained in Example 15 in the same manner as described in Example 21, (2) to give the title compound as a white needles; yield: 3.7 g (69.4%); mp 32.0°-36.5° C. $[\alpha]_D^{25}$: +12.8° (c2, CHCl$_3$)

$^1$H (NMR δppm (CDCl$_3$) 0.90 (6H, t, —(CH$_2$)$_6$C<u>H</u>$_3$ and —O(CH$_2$)$_4$C<u>H</u>$_3$), 1.30 (19H, m, —OCH$_2$(C<u>H</u>$_2$)$_5$CH$_3$,

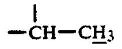

and —OCH$_2$(C<u>H</u>$_2$)$_3$CH$_3$), 3.53 (4H, m, —C<u>H</u>$_2$OC<u>H</u>$_2$—), 4.03 (2H, t, —OC<u>H</u>$_2$(CH$_2$)$_5$CH$_3$), 5.33 (1H, m,

6.97 (2H, d, J=8 Hz,

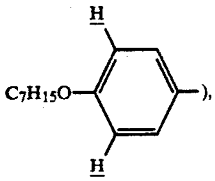

7.30(2H, d,

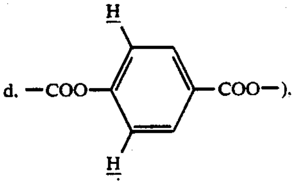

8.13(4H, d, J=8Hz,

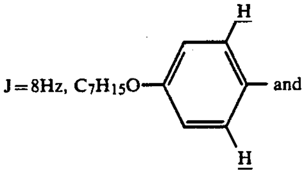

and

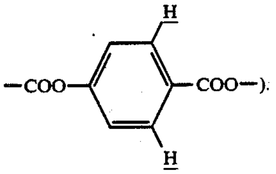

IR (Neat) νcm−1: 2930, 2855, 1735, 1720, 1600

Anal. calcd. for $C_{29}H_{40}O_6$: C%, 71.87; H%, 8.32; Found: C%, 71.89, H%, 8.30.

EXAMPLE 28

Synthesis of S(+)-1-Propyloxy-2-proply 4-(4-heptyloxybenzoyloxy)benzoate (Compound [II], m'=7, n=3)

Using 4-heptyloxybenzoic acid (3.07 g, 13 mmol) obtained in Example 27, (1), 4-heptyloxybenzoyl chloride was produced in the same manner as described in Example 21, (2), and then reacted with S(+)-1-propyloxy-2-propyl 4-hydroxybenzoate (2.6 g, 11 mmol) obtained in Example 16 in the same manner as described in Example 21, (2) to give the title compound as a white needles; yield: 3.3 g (65.7%); mp 46.2°-49.2° C. $[\alpha]_D^{25}$: +11.9° (c2, CHCl$_3$)

$^1$H NMR δppm (CDCl$_3$) 0.87 (6H, t, —(CH$_2$)$_6$C<u>H</u>$_3$ and —OCH$_2$CH$_2$C<u>H</u>$_3$), 1.30 (15H, m, —OCH$_2$(C<u>H</u>$_3$)$_5$CH$_3$,

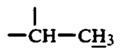

and $—OCH_2CH_2CH_3$), 3.47 (4H, m, $—CH_2OCH_2—$), 4.00 (2H, t, $—OCH_2(CH_2)_5CH_3$), 5.27 (1H, m, —CH—), 6.87 (2H, d, J=8 Hz,

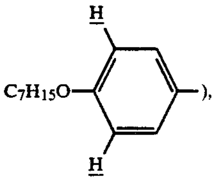

7.20(2H, d, J=8Hz, 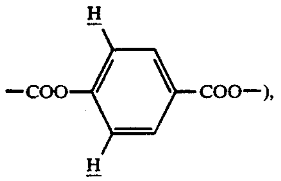

8.03(2H, d, J=8Hz, 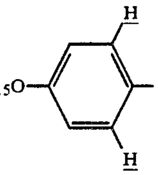 and

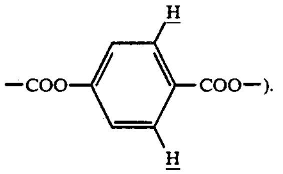

IR (Neat) $\nu cm^{-1}$: 2945, 2860, 1735, 1720, 1605.

Anal. calcd. for $C_{27}H_{36}O_6$: C%, 71.03; H%, 7.95; Found C%, 71.07, H%, 7.86.

EXAMPLE 29

Synthesis of S(+)-1-Ethyloxy-2-propyl 4-(4-heptyloxybenzoyloxy)benzoate (Compound [II], m'=7, n=2)

Using 4-heptyloxybenzoic acid (3.07 g, 13 mmol) obtained in Example 27, (1), 4-heptyloxybenzoyl chloride was produced in the same manner as described in Example 21, (2) and then reacted with S(+)-1-ethyloxy-2-propyl 4-hydroxybenzoate (2.5 g, 11 mmol) obtained in Example in the same manner as described in Example 21, (2) to give the title compound as a white leaflets; yield: 3.3 g (67.8%); mp 41.2°-44.3° C. $[\alpha]_D^{25}$: +13.6° (c2, $CHCl_3$)

$^1H$ NMR δppm ($CDCl_3$) 0.90 (6H, t, $—(CH_2)_6CH_3$ and $—OCH_2CH_3$), 1.33 (13H, m, $—OCH_2(CH_2)_5CH_3$ and

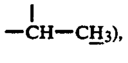

3.57 (4H, m, $—CH_2OCH_2$), 4.03 (2H, t, $—OCH_2(CH_2)_5CH_3$), 6.97 (2H, d, J=8 Hz,

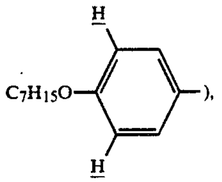

7.27(2H, d, J=8Hz, 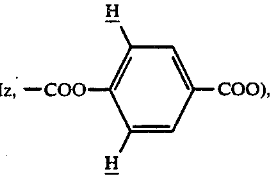

8.13(4H, d, J=8Hz, 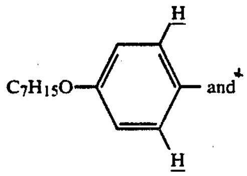 and

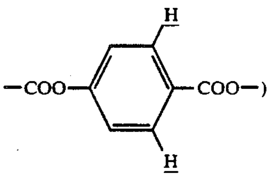

IR (Neat) $\nu cm^{-1}$: 2925, 2855, 1735, 1715, 1605.

Anal. calcd. for $C\%_{26}H_{34}O$: C%, 7.056; H%, 7.74; Found: C%, 70.67, H%, 7.63.

EXAMPLE 30

Synthesis of S(+)-1-Ethyloxy-2-propyl 4-(4-pentyloxybenzoyloxy)benzoate (Compound [II], m'=5, n=2)

(1) Synthesis of 4-Pentyloxybenzoic acid

To a solution of pentyl brimde (25 g, 0.17 mol), potassium carbonate (20.8 g) and potassium iodide (25 g) in acetone (200 ml), ethyl p-hydroxybenzoate (25 g, 0.15 mol) was added and stirring was continued for 12 h under reflux. After cooling, the reaction mixture was filtered to remove inorganic materials, and evaporated. The residue was taken up in $CH_2Cl_2$ (300 ml), washed with $H_2O$, dried over $MgSO_4$ and evaporated to give a colorless viscous oil (30 g) as a residue. The residue was solidified when cooled; mp 30.5°-34.0° C. Then the residue was stirred in $H_2O$ (120 ml) and ethanol (50 ml) containing sodium hydroxide (7.4 g) for 4 h under reflux. After cooling, the reaction mixture was acidified with hydrochloric acid, the resultant precipitate was filtered, washed with $H_2O$ and recrystallized from ethanol to give the title compound as a white needles; yield: 18.0 g (70.3%); mp 123.0°-124.5° C.

$^1H$ NMR δppm ($CDCl_3$—CMSO—$d_6$) 0.90 (3H, t, J=6 Hz, $—CH_2CH_3$), 1.23-1.96 (6H, m, $—CH_2(CH_2)_3CH_3$), 4.03 (2H, t, J=7 Hz, Ar—$OCH_2$—), 6.97 (2H, d, J=9Hx, Ar3-H 5-H), 7.95 (2H, d, J=9 Hz, Ar2-H 6-H), 12.50 (1H, bs, —COOH—)

IR (KBr) $\nu cm^{-1}$: 2940, 2860, 2650, 2530, 1670, 1605.

(2) Synthesis of S(+)-1-Ethyloxy-2-propyl 4-(4-pentyloxybenzoyloxy)benzoate (Compound [II], m'=5, n=2)

To a solution of 4-pentyloxybenzoic acid (4.0 g, 19 mmol) obtained in above (1) in 1,2-dichlorocthane, thionyl chloride (4.0 g) was added dropwise at 50°-60° C., and then stirring was continued for 2 h under reflux. The mixture was evaporated to dryness and the resultant residue was suspended in pyridine (50 ml). To this solution, S(+)-1-ethyloxy-2-propyl 4-hydroxybenzoate (4.0 g, 17 mmol) obtained in Example 17 was added dropwise at 20°-25° C. and stirred for 12 h at 20°-25° C. The reaction mixture was concentrated, diluted with $H_2O$ and extracted with $CH_2Cl_2$. The organic layer was separated, washed with $H_2O$, dried over $MgSO_4$, and evaporated. The resultant residue (13 g) was chromatographed on silica gel (Wako Gel C-200) with n-hexane/ethyl acetate (20:1) as eluent to give a pale yellow solid (6.1 g). The solid was recrystallized twice from ethanol to give the title compound as a white leaflets; yield: 3.1 g (57.0%); mp 64.0°-68.0° C.

$[\alpha]_D^{25}$: +12.3° (c2, $CHCl_3$).

$^1H$ NMR δppm ($CDCl_3$) 0.90-2.00 (15H, m, $—CH_2(CH_2)_3C\underline{H}_3$, $—CH—C\underline{H}_3$ and $—OCH_2C\underline{H}_3$), 3.33-3.73 (4H, m, $—C\underline{H}_2OC\underline{H}_2—$), 4.00 (2H, t, J=6 Hz, Ar-$OC\underline{H}_2$—), 5.06-5.53 (1H, m,

6.83-7.33 (4H, m,

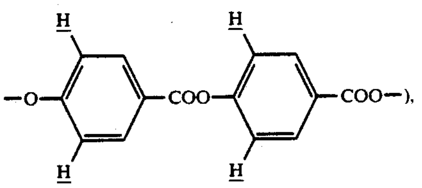

8.00-8.12(4H, m, 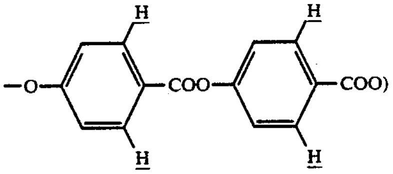

IR (Kbr) νcm$^{-1}$: 2900, 2850, 1720, 1610.

Anal. calcd. for $C_{24}H_{30}O_6$: C%, 69.54; H%, 7.29; Found: C%, 69.59; H%, 7.33.

EXAMPLE 31

Synthesis of S(+)-1-Ethyloxy-2-propyl 4-{4-(4-decyloxyphenyl)benzoyloxy}benzoate (Compound [IV], m=10, n=2)

(1) Synthesis of 4-Decyloxy-1,1'-biphenyl

4-Hydroxy-1,1'-biphenyl (61.3 g, 0.36 mol) and decyl bromide (218 g, 0.72 mol) were heated at 80° C. To this solution, a 50% potassium hydroxide aqueous solution (57 g) was added dropwise at 80° C. and then stirring was continued for 6 h at the same temperature. After cooling, the mixture was diluted with ethyl acetate, the organic layer was separated, washed with $H_2O$ and dried over $MgSO_4$. The solvent was removed under reduced pressure and the resultant residue was recrystallized from a mixed solvent of n-hexane and ethyl acetate to give the title compound as a white crystals; yield: 70 g (62.6%); mp 70.0°-73.0° C.

(2) Synthesis of 4-Acetyl-4'-decyloxy-1,1'-biphenyl

To a solution of 4-decyloxy-1,1'-biphenyl (15.5 g, 0.05 mol) obtained in above (1) and aluminum chloride (7.6 g) in carbon disulfide, acetyl chloride (4 g, 0.054 mol) was added dropwise at 20°-25° C., and stirring was continued for 2 h under reflux. After cooling, the reaction mixture was poured into 6N hydrochloric acid (100 ml), concentrated to remove carbon disulfide, and extracted with ethyl acetate. The organic extract was washed with $H_2O$, dried over $MgSO_4$, evaporated under reduced pressure and the resultant residue (18.5 g) was chromatographed on silica gel (Wako Gel C-200) with n-hexane/ethyl acetate (4:1) as eluent to give the title compound as a white crystals; yield: 4.5 g (25.5%); mp 101.8°-103.5° C. (the 1st mp), 121.0°-124.0° C. (the 2nd mp).

$^1H$ NMR δppm ($CDCl_3$) 0.90 (3H, t, J=6 Hz, $—(CH_2)_9C\underline{H}_3$), 1.10-2.10 (16H, m, $—CH_2(C\underline{H}_2)_8CH_3$), 2.60 (3H, s, $—COC\underline{H}_3$), 4.00 (2H, t, J=6 Hz, $—C\underline{H}_2O—$), 6.97 (2H, d, J=9 Hz, Ar3'-H 5'-H), 7.47-7.67 (4H, m, Ar2-H 6-H 2'-H 6'-H), 7.97 (2H, d, J=9 Hz, Ar3-H 5-H).

IR (KBr) νcm$^{-1}$: 2980, 2910, 1690, 1610.

(3) Synthesis of 4-(4-Decyloxyphenyl)benzoic acid

To a solution of 4-acetyl-4'-decyloxy-1,1'-biphenyl (4.2 g, 0.012 mol) in 1,4-dioxane (20 ml), an aqueous solution of sodium hypobromite (40 ml) [freshly prepared from sodium hydroxide (7.9 g) and bromine (7.1 g)] was added dropwise at 20°-25° C., and stirring was continued for 2 h at 40° C. After cooling, sodium bisulfite was added to destroy excess sodium hypobromite and the mixture was acidified with hydrochloric acid. The resultant precipitate was filtered, washed with $H_2O$ and dried to give the title compound as a white amorphous powder; yield: 3.5 g (90.1%); mp 245.5°-250.0° C.

$^1H$ NMR δppm ($CDCl_3$) 0.87 (3H, t, J=6 Hz, $—(CH_2)_8C\underline{H}_3$), 1.10-2.07 (16H, m, $—CH_2(C\underline{H}_2)_8CH_3$), 4.17 (2H, 5, J=6 Hz, $—C\underline{H}_2O—$), 7.10 (2H, d, J=9 Hz,

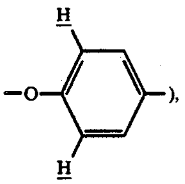

7.63-7.83(4H, m, 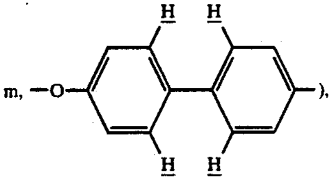

-continued 8.10(2H, d, J=9Hz, 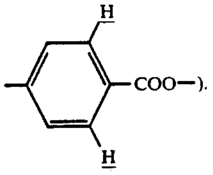

IR (KBr) $\nu cm^{-1}$: 2940, 2860, 2680, 2560, 1685, 1605.

(4) Synthesis of S(+)-1-Ethyloxy-2-propyl 4-{4-(4-decyloxyphenyl)benzoyloxy}benzoate. (Compound [IV], m=10, n=2)

To a solution of 4-(4-decyloxyphenyl)benzoic acid (5.2 g, 14.7 mmol) obtained in above (3) in 1,2-dichloroethane, thionyl chloride (5.2 g) was added dropwise at 50°-60° C., and then stirring was continued for 2 h under reflux. The mixture was evaporated to dryness and the resultant residue was suspended in pyridine (120 ml). To this solution, S(+)-1-ethyloxy-2-propyl 4-hydroxybenzoate (3 g, 13.4 mmol) obtained in Example 17 was added dropwise at 20°-25° C. and stirred for 4 h at 40° C. The reaction mixture was concentrated, diluted with $H_2O$ and extracted with $CH_2Cl_2$. The organic layer was separated, washed with $H_2O$, dried over $MgSO_4$, and evaporated. The resultant residue was chromatographed on silica gel (Wako Gel C-200) with n-hexane/ethyl acetate (3:1) as eluent to give a pale yellow solid (6.0 g). The solid was recrystallized twice from ethanol to give the title compound as a white microneedles; yield: 4.3 g (58.9%); mp 70.5°-74.0° C. (the 1st mp), 157.5°-158.5° C. (the 2nd mp). $[\alpha]_D^{25}$: +10.0° (c2, $CHCl_3$).

$^1H$ NMR δppm ($CDCl_3$) 0.87 (3H, t, J=6 Hz, $-(CH_2)_9C\underline{H}_3$), 1.07-1.87 (22H, m, $-CH_2(C\underline{H}_2)_7CH_3$,

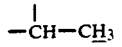

and $-OCH_2C\underline{H}_3$), 3.40-3.73 (4H, m, $-C\underline{H}_2OC\underline{H}_2-$), 4.00 (2H, t, J=6 Hz, Ar$-OC\underline{H}_2-$), 5.10-5.47 (1H, m, J=6 Hz,

6.90-8.23 (12H, m, ArH).

IR (KBr) $\nu cm^{-1}$: 2930, 2850, 1740, 1720, 1605

Anal. calcd. for $C_{35}H_{44}O_6$: C%, 74.97; H%, 7.91; Found: C%, 75.11: H%, 7.78.

EXAMPLE 32

Synthesis of S(+)-1-Hethyloxy-2-propyl 4-(4-decyloxybenzoyloxy)benzoate (Compound [II], m'=10, n=1)

Using 4-decyloxybenzoic acid (3.5 g, 12.5 mmol) obtained in Example 21, (1), 4-decyloxybenzoyl chloride was produced in the same manner as described in Example 21, (2), and then reacted with S(+)-1-methyloxy-2-propyl 4-hydroxybenzoate (2.3 g, 11 mmol) obtained in Example 18 in the same manner as described in Example 21, (2) to give the title compound as a colorless viscous oil; yield: 4.0 g (77.2%). $[\alpha]_D^{25}$: +9.2° (c2, $CHCl_3$)

$^1H$ NMR δppm ($CDCl_3$) 0.87 (3H, t, J=6 Hz, $-(CH_2)_8C\underline{H}_3$), 1.07-2.03 (19H, m, $-CH_2(C\underline{H}_2)_8CH_3$ and

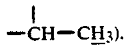

3.17 (3H, s, $OC\underline{H}_3$), 3.57 (2H, d, J=6 Hz, $-C\underline{H}_2OCH_3$), 4.00 (2H, t, J=6 Hz, Ar$-OC\underline{H}_2-$), 5.07-5.57 (1H, m, J=6 Hz,

6.93 (2H, d,J=9 Hz,

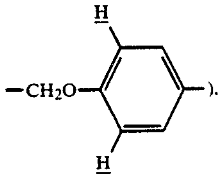

7.27(2H, d, J=9Hz, 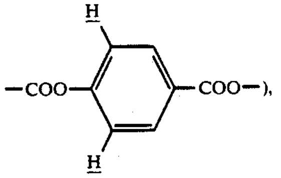

8.13(4H, d, J=9Hz, 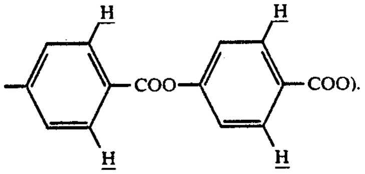

IR (Neat) $\nu cm^{-1}$: 2920, 2850, 1740, 1720, 1605.

Anal. calcd. for $C_{28}H_{38}O_6$: C%, 71.46; H%, 8.14; Found: C%, 71.58, H%, 8.01.

EXAMPLE 33

Synthesis of S(+)-1-Decyloxy-2-propyl 4-(4-docosyloxybenzoyloxy)benzoate (Compound (II], m'=22, n=10)

(1) Synthesis of 4-Docosyloxybenzoic acid

To a solution of docosyl bromide (25 g, 0.064 mol), potassium carbonate (9.0 g) and sodium iodide (9.6 g) in acetone (150 ml), ethyl p-hydroxybenzoate (10.2 g, 0.061 mol) was added, and then reacted for 12 h under reflux with stirring. After cooling, the reaction mixture was filtered to remove inorganic materials, taken up in $H_2O$ (500 ml), and extracted with $CH_2Cl_2$(3×100 ml). The organic layer was separated, washed with $H_2O$, dried over $MgSO_4$, and evaporated to dryness. The resultant residue was recrystallized from ethyl acetate to give ethyl 4-docosyloxybenzoate (27 g) as a white crystals; mp 56.5°-59.5° C. Then ethyl 4-docosyloxybenzoate (27 g) was stirred in $H_2O$ (120 ml) and ethanol (150 ml) containing sodium hydroxide (4.6 g) for 6 h under reflux. After cooling, the reaction mixture was acidified with hydrochloric acid, the resultant precipitate was filteted, washed with $H_2O$ and recrystallized from acetic acid to give the title compound as a white needles; yield: 18.5 g (72.7%); mp 99.0°-101.5° C.

$^1$H NMR δppm ($CDCl_3$-DMSO-$d_6$) 0.87 (3H, t, J=6 Hz, —$(CH_2)_{20}C\underline{H}_3$), 1.00-2.06 (40 H, m, —$OCH_2(C\underline{H}_2)_{20}$—$CH_3$), 4.07 (2H, t, J=6 Hz, —$OC\underline{H}_2(CH_2)_{20}$—), 6.83 (2H, d, J=9 Hz, Ar3-H 5-H), 8.00 (2H, d, J=9 Hz, Ar2-H 6-H), 12.37 (1H, bs, —COO$\underline{H}$).

IR (KBr) νcm$^{-1}$: 2910, 2850, 1670, 1605.

(2) Synthesis of S(+)-1-Decyloxy-2-propyl 4-(4-docosyloxybenzoyloxy)benzoate (Compound [II], m'=22, n=10)

To a solution of 4-docosyloxybenzoic acid (4.4 g, 10 mmol) obtained in above (1) in toluene (30 ml), thionyl chloride (2.4 g) was added dropwise at 50°-60° C., and then stirring was continued for 1 h at 90°-100° C. The mixture was concentrated to dryness and the resultant residue was suspended in pyridine (35 ml). To this solution, S(+)-1-decyloxy-2-propyl 4-hydroxybenzoate (3.0 g, 9 mmol) obtained in Example 19 was added dropwise at 20°-25° C. and stirred for 3 h at the same temperature. The reaction mixture was concentrated, diluted with $H_2O$ and extracted with $CH_2Cl_2$. The organic layer was separated, washed with $H_2O$, dried over $MgSO_4$, and evaporated. The resultant residue (7.5 g) was chromatographed on silica gel (Wako Gel C-200) with n-hexane/ethyl acetate (4:1) as eluent and further recrystallized twice from a mixed solvent of ethyl acetate and ethanol to give the title compound as a white microneedles; yield: 2.5 g (36.2%); mp 51.0°-59.5° C. $[\alpha]_D^{25}$: +6.8° (c2, $CHCl_3$)

$^1$H NMR δppm ($CDCl_3$) 0.87 (6H, t, J=6 Hz, —$O(CH_2)_{21}C\underline{H}_3$ and —$O(CH_2)_9C\underline{H}_3$), 1.03-1.97 (59H, m, —$OCH_2(C\underline{H}_2)_{20}CH_3$,

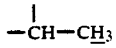

and —$OCH_2(C\underline{H}_2)_8CH_3$), 3.37-3.60 (4H, m, —$C\underline{H}_2OC\underline{H}_2$—), 4.02 (2H, t, J=6 Hz, Ar—$OC\underline{H}_2$—), 5.07-5.43 (1H, m, J=6 Hz,

6.93(2H, d, J=9Hz,

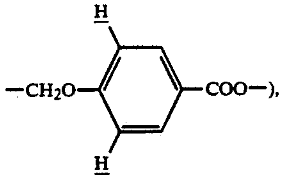

7.27(2H, d, J=9Hz,

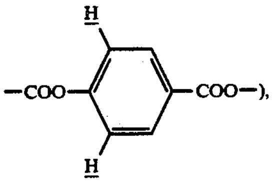

8.07(4H, d, J=9Hz,

-continued

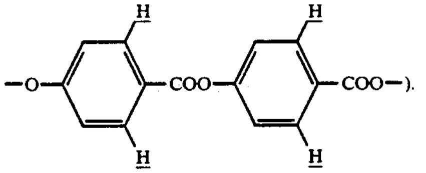

IR (KBr) νcm$^{-1}$: 2940, 2870, 1740, 1720, 1610.

Anal. calcd. for $C_{49}H_{80}O_6$: C%, 76.92; H%, 10.54; Found: C%, 77.09; H%, 10.38.

EXAMPLE 34

Synthesis of S(+)-1-Ethyloxy-2-propyl 4-{4-(4decyloxybenzoyloxy)phenyl}benzoate (Compound [III], m=10, n=2)

Using 4-decyloxybenzoic acid (4.2 g, 15 mmol) obtained in Example 21, (1), 4-decyloxybenzoyl chloride was produced in the same manner as described in Example 21, (2), then reacted with S(+)-1-ethyloxy-2-propyl 4-(4-hydroxyphenyl)benzoate (4.1 g, 13.5 mmol) obtained in Example 20 in the same manner as described in Example 21, (2) and further recrystallized twice from a mixed solvent of ethyl acetate and ethanol to give the title compound as a white amorphous powder; yield: 5.2 g (68.7%); mp 56.0°-58.5° C. (the 1st mp), 139.5°-140.5° C. (the 2nd mp); $[\alpha]_D^{25}$: +10.8° (c2, $CHCl_3$).

$^1$H NMR δppm ($CDCl_3$) 0.87 (3H, t, J=6 Hz, —$(CH_2)_8C\underline{H}_3$), 1.07-1.90 (22H, m, —$(C\underline{H}_2)_8CH_3$,

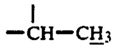

and —$OCH_2C\underline{H}_3$), 3.37-3.73 (4H, m, —$C\underline{H}_2OC\underline{H}_2$—), 4.00 (2H, t, J=6 Hz, Ar—$OC\underline{H}_2$—), 5.07-5.47 (1H, m, J=6 Hz,

6.87-8.20 (12H, m, ArH).

IR (KBr) νcm$^{-1}$: 2900, 2820, 1720, 1605.

Anal. calcd. for $C_{35}H_{44}O_6$: c%, 74.94; H%, 7.91; Found: C%, 75.12; H%, 7.76.

EXAMPLE 35

Synthesis of S(+)-1-Ethyloxy-2-propyl 4-{4-[4-(4decyloxyphenyl)benzoyloxy]phenyl}benzoate (Compound [I], k=2, l=2, m=10, n=2)

Using 4-(4-decyloxyphenyl)benzoic acid (2.0 g, 5.6 mmol) obtained in Example 31, (3), 4-(4-decyloxyphenyl)benzoyl chloride was produced in the same manner as described in Example 31, (4), then reacted with S(+)-1-ethyloxy-2-propyl 4-(4-hydroxyphenyl)benzoate (1.7 g, 5.6 mmol) obtained in Example 20 in the same manner as described in Example 31, (4) and further recrystallized twice from a mixed solvent of n-hexane and ethyl acetate to give the title compound as a white amorphous powder; yield: 1.5 g (42.1%); mp 102.0°-104.0° C. (the 1st mp), 258.0°-259.0° C. (the 2nd mp); $[\alpha]_D^{25}$: +10.3° (c2, $CHCl_3$).

$^1$H NMR δppm ($CDCl_3$) 0.87 (3H, t, J=6 Hz, —$(CH_2)_8C\underline{H}_3$), 1.07-1.90 (22H, m, —$(C\underline{H}_2)_8CH_3$,

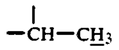

and $—OCH_2CH_3$), 3.47–3.73 (4H, m, $—CH_2OCH_2—$), 4.07 (2H, t, J=6 Hz, $Ar—OCH_2—$), 6.98–8.27 (16H, m, ArH).

IR (KBr) $\nu cm^{-1}$: 2920, 2850, 1735, 1720, 1605.

Anal. calcd. for $C_{41}H_{48}O_6$: C%, 77.33; H%, 7.60,; Found: C%, 77.39; H%, 7.51.

APPLICATION EXAMPLE 1

Phase transition temperatures of the liquid crystal compounds obtained in Examples 21 to 35 according to the present invention were measured by using a differential scanning calorimeter and a polarization microscope and are shown in Table 1.

In Table 1, a black point means the presence of a phase. Figures show transition temperatures and those in parentheses show the values at a time of temperature decrease. Further, abbreviations in Table 1 have the following meaning:

| | |
|---|---|
| Cr: | crystalline phase |
| $S_4$, $S_3$ | unidentified smectic phases |
| $S_C$*: | a chiral smectic C phase |
| $S_A$: | a smectic A phase |
| N: | a nematic phase |
| I: | an isotropic phase |

TABLE 1

| Structure | Phase transition temperature (°C.) | | | | | | |
|---|---|---|---|---|---|---|---|
| | $C_r$ | $S_4$ | $S_3$ | $S_C$* | $S_A$ | N | I |
| 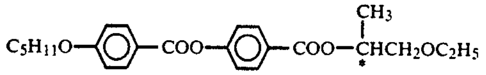 | ·65 | | | | | | · |
| 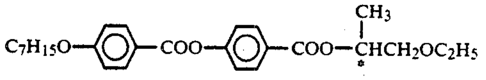 | ·43 | | | | (·28) | | · |
| 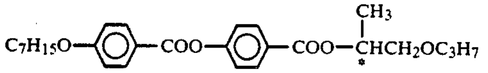 | ·48 | | | | (·28) | | · |
| 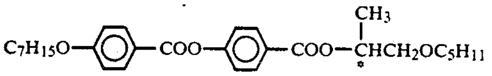 | ·32 | | | | (·21) | | · |
| 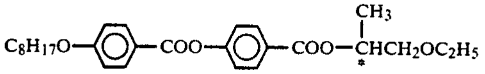 | ·43 | | | | (·32) | | · |
| 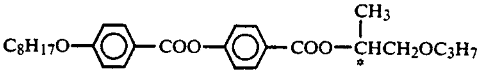 | ·37 | | | | (·32) | | · |
| 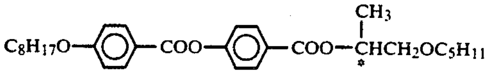 | ·20 | | | | ·28 | | · |
| 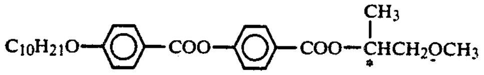 | ·14 | | | | ·20 | | · |
| 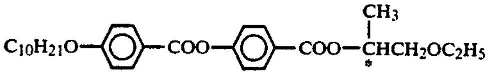 | ·34 | | | (·21) | (·34) | | · |
| 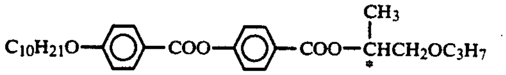 | ·35 | | | (·21) | (·32) | | · |
| 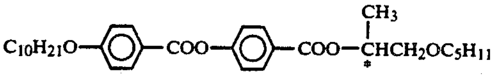 | ·35 | | | (·21) | (·32) | | · |
| 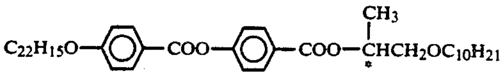 | ·54 | | | | | | · |
| 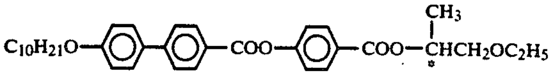 | ·67.1 | (·50.5) | ·99.1 | ·128.2 | ·155.4 | | · |

TABLE 1-continued

| Structure | Phase transition temperature (°C.) | | | | | | |
|---|---|---|---|---|---|---|---|
| | $C_r$ | $S_4$ | $S_3$ | $S_{C^*}$ | $S_A$ | N | I |
| 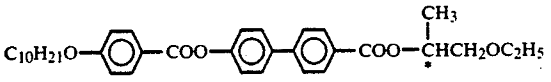 | ·54.2 | | | ·100 | ·138 | | · |
| 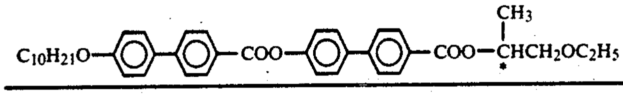 | | ·120 | ·150 | ·197 | ·255 | | · |

As explained above, the liquid crystal compounds of the present invention show a liquid crystal phase at near room temperature and temperatures higher than room temperature, and thus can be applied as ferroelectric liquid crystal materials operable at room temperature and as components constituting such ferroelectric liquid crystal materials. Further, the liquid crystal compounds of the present invention have a chemically stable molecular structure, can provide larger spontaneous polarization due to having an asymmetric carbon atom near an aromatic ring and are excellent in practical use. In addition, processes used in the present invention are effective for producing the liquid crystal compounds and intermediates thereof, said liquid crystal compounds showing a liquid crystal phase at near room temperature and higher.

What is claimed is:

1. A liquid crystal compound according to claim 1, which is represented by the formula:

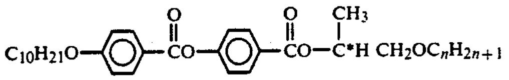

wherein n is an integer of 2 to 5.

2. A liquid crystal compound according to claim 1, which is represented by the formula:

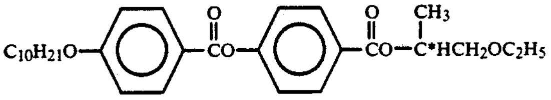

3. A liquid crystal compound according to claim 1, which is represented by the formula:

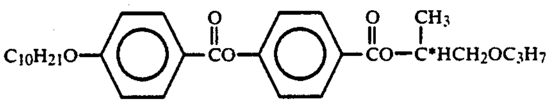

4. A liquid crystal compound according to claim 1, which is represented by the formula:

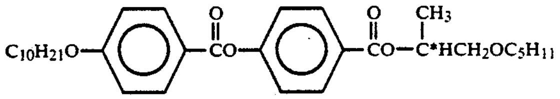

* * * * *